United States Patent
Farrell et al.

(10) Patent No.: US 12,024,515 B2
(45) Date of Patent: Jul. 2, 2024

(54) KIFUNENSINE DERIVATIVES

(71) Applicant: University of Kansas, Lawrence, KS (US)

(72) Inventors: Mark Patrick Farrell, Lawrence, KS (US); Suresh Eknath Kurhade, Lawrence, KS (US); Patrick Andrew Ross, Lawrence, KS (US); Jack Douglas Weiner, Overland Park, KS (US); Fei Philip Gao, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 18/272,252

(22) PCT Filed: Jan. 22, 2022

(86) PCT No.: PCT/US2022/013431
§ 371 (c)(1),
(2) Date: Jul. 13, 2023

(87) PCT Pub. No.: WO2022/159781
PCT Pub. Date: Jul. 28, 2022

(65) Prior Publication Data
US 2023/0391777 A1    Dec. 7, 2023

Related U.S. Application Data

(60) Provisional application No. 63/140,406, filed on Jan. 22, 2021, provisional application No. 63/140,363, filed on Jan. 22, 2021.

(51) Int. Cl.
*C07D 471/04* (2006.01)
*A61K 31/437* (2006.01)
*A61K 39/395* (2006.01)
*C07D 491/22* (2006.01)

(52) U.S. Cl.
CPC .......... *C07D 471/04* (2013.01); *A61K 31/437* (2013.01); *A61K 39/3955* (2013.01); *C07D 491/22* (2013.01)

(58) Field of Classification Search
CPC ..... C07D 471/04; A61K 31/437; A61P 35/00; A61P 35/02
USPC .......................................... 546/121; 514/300
See application file for complete search history.

(56) References Cited

U.S. PATENT DOCUMENTS 5,672,662 A    9/1997    Harris et al.

FOREIGN PATENT DOCUMENTS

| WO | WO-2011/151493 A1 | 12/2011 | |
|---|---|---|---|
| WO | WO-2017/117269 A1 | 7/2017 | |
| WO | WO-2019/243672 A1 | 12/2019 | |
| WO | WO 2021/123506 A1 * | 6/2021 | ............. A61K 47/68 |

OTHER PUBLICATIONS (PURCHEM.)[(5R,6R,7S,8R,8aS)-1-(6-acetamidohexyl)-6,7,8-triaceryloxy-2,3-dioxo-6,7,8,8A totrahydro-5H-i midazo[1,2-a]pyridin-5-yl]methyl acetate. SID 23792509. Pubchem Entry (online)., National Center for Biotechnology Information. May 5, 2011 [retrieved on Mar. 3, 2021). Retrieved from the Internet [URL: https://pubchem.ncbi.nlm.nih.gov/substance/23792509]; p. 2.
International Search Report & Written Opinion of the International Searching Authority issued in PCT Application No. PCT/US2022/013431, mailed Apr. 25, 2022.
Bonavida, Benjamin, "Postulated mechanisms of resistance of B-cell non-Hodgkin lymphoma to rituximab treatment regimens: strategies to overcome resistance", Seminars in Oncology, Oct. 2014, vol. 41, No. 5, pp. 667-677, PubMed PMID: 25440611; PMCID: PMC4254685.
Bray et al., "Global cancer statistics 2018: GLOBOCAN estimates of incidence and mortality worldwide for 36 cancers in 185 countries" CA: A Cancer Journal for Clinicians, 2018, vol. 68, pp. 394-424, PubMed PMID: 30207593.
Czuczman et al., "Acquirement of rituximab resistance in lymphoma cell lines is associated with both global CD20 gene and protein down-regulation regulated at the pretranscriptional and posttranscriptional levels", Clinical Cancer Research, Mar. 1, 2008, vol. 14, No. 5, pp. 1561-1570, PubMed PMID: 18316581.
Davis et al., "Therapy of B-cell lymphoma with anti-CD20 antibodies can result in the loss of CD20 antigen expression", Clinical Cancer Research, Mar. 1999, vol. 5, No. 3, pp. 611-615, PubMed PMID: 10100713.
Ginaldi et al., "Levels of expression of CD19 and CD20 in chronic B cell leukaemias", Journal of Clinical Pathology, 1998, vol. 51, No. 5, pp. 364-369, PubMed PMID: 9708202; PMCID: PMC500695.
Golay et al., "CD20 levels determine the in vitro susceptibility to rituximab and complement of B-cell chronic lymphocytic leukemia: further regulation by CD55 and CD59" Blood, Dec. 1, 2001, vol. 98, No. 12, pp. 3383-3389, PubMed PMID: 11719378.
Hiraga et al., "Down-regulation of CD20 expression in B-cell lymphoma cells after treatment with rituximab-containing combination chemotherapies: its prevalence and clinical significance", Blood, May 13, 2009, vol. 113, No. 20, pp. 4885-4893, PubMed PMID: 19246561.

(Continued)

*Primary Examiner* — Charanjit Aulakh
(74) *Attorney, Agent, or Firm* — Foley & Lardner LLP

(57) ABSTRACT

The present disclosure relates to compounds according to Formula I (I) or a pharmaceutically acceptable salt and/or solvate thereof, as well as compositions including such compounds and uses thereof, where $R^1$ is an unsubstituted $C_1$-$C_{12}$ alkyl; and $R^2$, $R^3$, and $R^4$ are each independently H or —C(O)—(unsubstituted $C_1$-$C_{12}$ alkyl). Among other things, the present disclosure evidences that the significant upregulation of CD20 by the inhibition of a-mannosidase enzymes by compounds of the present technology potentiates the activity of anti-CD20 mAbs and importantly sensitize cell lines that are resistant to the action of these antibodies.

21 Claims, 9 Drawing Sheets

(56) References Cited

OTHER PUBLICATIONS

Jilani et al., "Transient down-modulation of CD20 by rituximab in patients with chronic lymphocytic leukemia", Blood, Nov. 15, 2003, vol. 102, No. 10, pp. 3514-3520, PubMed PMID: 12893761.

Kennedy et al., "Incidence and nature of CD20-negative relapses following rituximab therapy in aggressive B-cell non-Hodgkin's lymphoma: a retrospective review" British Journal of Haematology, 2002, vol. 119, No. 2, pp. 412-416, PubMed PMID: 12406079.

Khouri et al., "Concurrent administration of high-dose rituximab before and after autologous stem-cell transplantation for relapsed aggressive B-cell non-Hodgkin's lymphomas", Journal of Clinical Oncology, Apr. 1, 2005, vol. 23, No. 10, pp. 2240-2247, PubMed PMID: 15800314.

Khouri et al., "Eight-year experience with allogeneic stem cell transplantation for relapsed follicular lymphoma after nonmyeloablative conditioning with fludarabine, cyclophosphamide, and rituximab", Blood, Jun. 15, 2008, vol. 111, No. 12, pp. 5530-5536, PubMed PMID: 18411419; PMCID: PMC4624452.

Kinoshita et al., "CD20-negative relapse in B-cell lymphoma after treatment with Rituximab", Journal of Clinical Oncology, Dec. 1998, vol. 16, No. 12, p. 3916. PubMed PMID: 9850038.

Mankaï et al., "Purine-rich box-1-mediated reduced expression of CD20 alters rituximab-induced lysis of chronic lymphocytic leukemia B cells", Cancer Research, Sep. 15, 2008, vol. 68, No. 18, pp. 7512-7519, PubMed PMID: 18794139.

McLaughlin et al., "Rituximab chimeric anti-CD20 monoclonal antibody therapy for relapsed indolent lymphoma: half of patients respond to a four-dose treatment program", Journal of Clinical Oncology, Aug. 1998, vol. 16, No. 8, pp. 2825-2833, PubMed PMID: 9704735.

Neumann, "Rituximab long-term maintenance therapy after autologous stem cell transplantation in patients with B-cell non-Hodgkin's lymphoma", Annals of Hematology, 2006, vol. 85, No. 8, pp. 530-534, PubMed PMID: 16639571.

Olejniczak et al., "Acquired resistance to rituximab is associated with chemotherapy resistance resulting from decreased Bax and Bak expression", Clinical Cancer Research, Mar. 1, 2008, vol. 14, No. 5, pp. 1550-1560, PubMed PMID: 18316580.

Payandeh et al., The applications of anti-CD20 antibodies to treat various B cells disorders,%u201D Biomedicine & Pharmacotherapy, 2019, vol. 109, pp. 2415-2426.

Pickartz et al., "Selection of B-cell chronic lymphocytic leukemia cell variants by therapy with anti-CD20 monoclonal antibody rituximab", Experimental Hematology, 2001, vol. 29, No. 12, pp. 1410-1416, PubMed PMID: 11750099.

Sarro et al., "Quantification of CD20 mRNA and protein levels in chronic lymphocytic leukemia suggests a post-transcriptional defect", Leukemia Research, 2010, vol. 34, No. 12, pp. 1670-1673, PubMed PMID: 20674973.

Silva et al., Glycans as Immune Checkpoints: Removal of Branched N-glycans Enhances Immune Recognition Preventing Cancer Progression%u201D,. Cancer Immunol Research, 2020, vol. 8, No. 11, pp. 1407-1425, doi: 10.1158/2326-6066.Cir-20-0264. PubMed PMID: 32933968.

Smith, Mitchell R. "Rituximab (monoclonal anti-CD20 antibody): mechanisms of action and resistance", Oncogene. 2003, vol. 22, No. 47, pp. 7359-7368, PubMed PMID: 14576843.

Tun et al., "Immunotherapy in Hodgkin and non-Hodgkin lymphoma: Innate, adaptive and targeted immunological strategies", Cancer Treatment Reviews, 2020, vol. 88, 102042. 10 pages, PubMed PMID: 32521386.

Van Meerten et al., "Complement-induced cell death by rituximab depends on CD20 expression level and acts complementary to antibody-dependent cellular cytotoxicity", Clinical Cancer Research, 2006, vol. 12, No. 13, pp. 4027-4035, PubMed PMID: 16818702.

\* cited by examiner

KIFUNENSINE DERIVATIVES

CROSS-REFERENCE TO RELATED APPLICATIONS

This application is a U.S. National Phase Application under 35 U.S.C. § 371 of International Application No. PCT/US2022/013431, filed on Jan. 22, 2022, which claims the benefit of and priority to U.S. Provisional Appl. No. 63/140,363, filed Jan. 22, 2021, and U.S. Provisional Appl. No. 63/140,406, filed Jan. 22, 2021, the contents of each of which are incorporated herein by reference in their entirety for any and all purposes.

U.S. GOVERNMENT SUPPORT

This invention was made with government support under GM113117 and GM110761 awarded by the National Institutes of Health. The government has certain rights in the invention.

FIELD

The present technology is directed to compounds, compositions, and methods related to kifunensine derivatives (also referred to herein as kifunensine analogs) and uses thereof.

SUMMARY

In an aspect, the present technology provides a compound according to Formula I

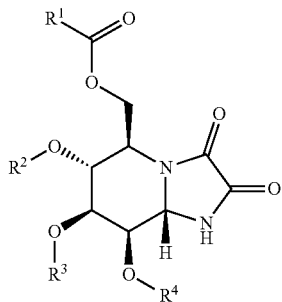

(I)

or a pharmaceutically acceptable salt and/or solvate thereof, where $R^1$ is an unsubstituted $C_1$-$C_{12}$ alkyl; and $R^2$, $R^3$, and $R^4$ are each independently H or —C(O)—(unsubstituted $C_1$-$C_{12}$ alkyl).

In an aspect, a composition is provided that includes a compound of any embodiment disclosed herein, a pharmaceutically acceptable carrier or one or more excipients, fillers or agents (collectively referred to hereafter as "pharmaceutically acceptable carrier" unless otherwise indicated and/or specified).

In a related aspect, a medicament for treating a B-cell malignancy in a subject is provided that includes a compound of any embodiment disclosed herein and optionally a pharmaceutically acceptable carrier.

In a related aspect, a pharmaceutical composition is provided that includes (i) an effective amount of a compound of any embodiment disclosed herein, wherein the effective amount of the compound is effective to treat a B-cell malignancy; and (ii) a pharmaceutically acceptable carrier.

In a related aspect, a pharmaceutical composition is provided that includes (i) an effective amount of a compound of any embodiment disclosed herein, where the compound is present in an amount effective to treat a B-cell malignancy when combined with an anti-CD20 monoclonal antibody; and (ii) a pharmaceutically acceptable carrier.

In further related aspects, the present technology provides methods including a compound of any aspect or embodiment disclosed herein and/or a composition of any embodiment disclosed herein and/or a medicament of any embodiment disclosed herein. Such methods include a method of treating a subject suffering from a B-cell malignancy, where the method includes administering to the subject an effective amount of a compound of any embodiment disclosed herein and an effective amount of an anti-CD20 monoclonal antibody. Such methods also include a method of producing high mannose glycoproteins, where such a method may include contacting a cell culture with a compound of any embodiment disclosed herein thus generating high mannose glycoproteins.

DETAILED DESCRIPTION

Figure 1A:
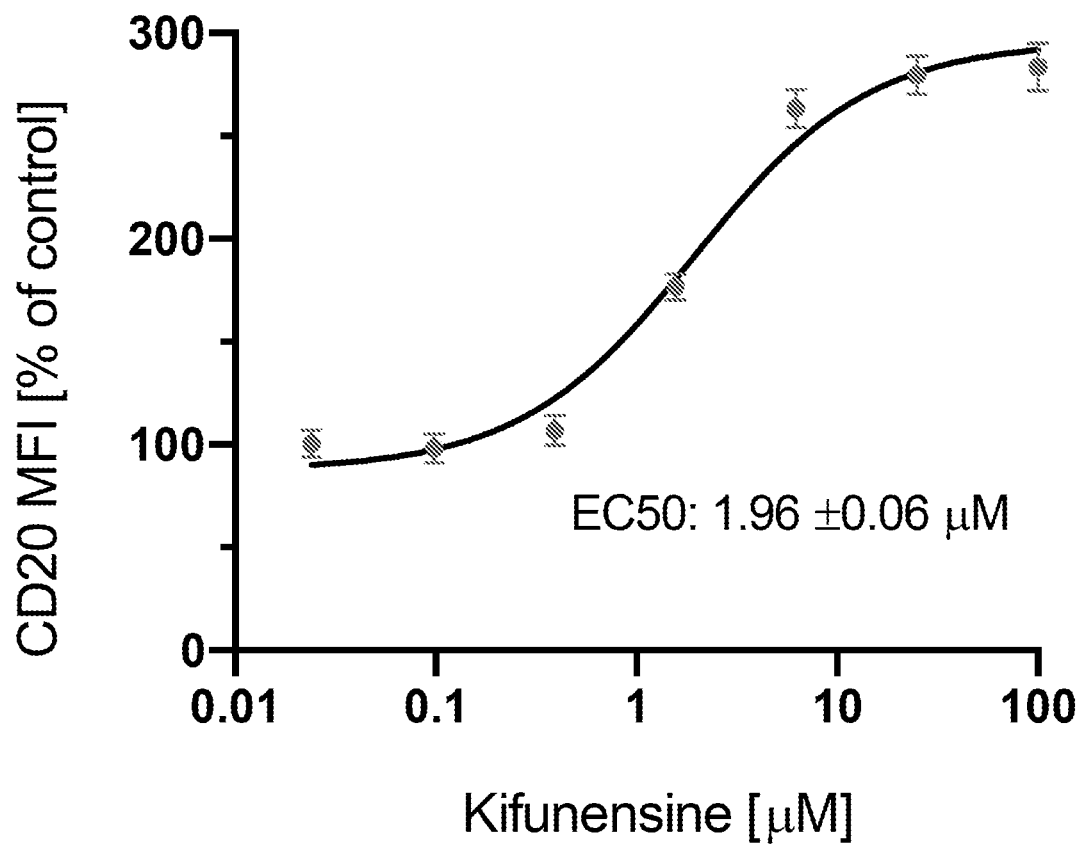
FIGS. 1A-1E relate to kifunensine ("Kif") induced expression of CD20. Raji cells were incubated with Kif for 48 hours and CD20 levels on the cell surface levels were analyzed by flow cytometry (FIG. 1A) and in whole cell lysate by western blotting (FIG. 1B). Raji cells were preincubated with Kif (25 µM), Swain (25 µM), DMJ (1 mM), and DIM (1 mM) or vehicle for 48 hours, and the cell surface levels of CD20 were analyzed by flow cytometry (FIG. 1C). Cells were incubated with Kif (25 µM) or vehicle for 48 hours and the cell surface levels of CD20 were analyzed by flow cytometry (FIG. 1D). Raji and rituximab resistant cells were incubated with Kif (25 µM) or vehicle for 48 hours and the cell surface levels of CD20 were analyzed by flow cytometry (FIG. 1E). Results are presented as a percentage of MFI of vehicle treated control cells (±SD). Statistical significance was determined with Kruskal-Wallis test, *$P<0.033$, $P<0.002$, **$P<0.001$, vs control.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would be understood to mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

The phrase "and/or" as used in the present disclosure will be understood to mean any one of the recited members individually or a combination of any two or more thereof—for example, "A, B, and/or C" would mean "A, B, C, A and B, A and C, B and C, or the combination of A, B, and C."

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; and nitriles (i.e., CN).

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH₃), —CH=C(CH₃)₂, —C(CH₃)=CH₂, —C(CH₃)=CH(CH₃), —C(CH₂CH₃)=CH₂, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, and —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Aryl groups may be substituted or unsubstituted. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted (e.g., tolyl) or substituted more than once. For example, mono-substituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. Heterocyclyl groups may be substituted or unsubstituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. The phrase includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolykazaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O—G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)-(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C($R^{94}$)=C($R^{95}$)N$R^{96}R^{97}$ and —N$R^{94}$C($R^{95}$)=C($R^{96}$)$R^{97}$, wherein $R^{94}$, $R^{95}$, $R^{96}$ and $R^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, A "hydroxyalkyl" group is a hydroxyl-substituted alkyl group, such as HO—CH$_2$—.

The term "imide" refers to —C(O)N$R^{98}$C(O)$R^{99}$, wherein $R^{98}$ and $R^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —C$R^{100}$(N$R^{101}$) and —N(C$R^{100}R^{101}$) groups, wherein $R^{100}$ and $R^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that $R^{100}$ and $R^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "pentafluorosulfanyl" refers to —SF$_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As understood by one of ordinary skill in the art, "molecular weight" (also known as "relative molar mass") is a dimensionless quantity but is converted to molar mass by multiplying by 1 gram/mole or by multiplying by 1 Da—for example, a compound with a weight-average molecular weight of 5,000 has a weight-average molar mass of 5,000 g/mol and a weight-average molar mass of 5,000 Da.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., Na$^+$, Li$^+$, K$^+$, Ca$^{2+}$, Mg$^{2+}$, Zn$^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism, and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

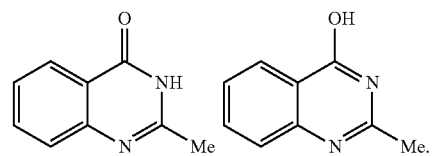

As another example, guanidines may exhibit the following isomeric forms in protic organic solution, also referred to as tautomers of each other:

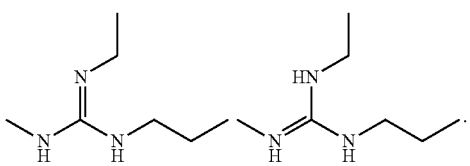

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Throughout this disclosure, various publications, patents and published patent specifications are referenced by an identifying citation. Also within this disclosure are Arabic numerals referring to referenced citations, the full bibliographic details of which are provided subsequent to the Examples section. The disclosures of these publications, patents and published patent specifications are hereby incorporated by reference into the present disclosure to more fully describe the present technology.

The Present Technology

Hematologic B cell malignancies, such as non-Hodgkin lymphoma (NHL) and chronic lymphocytic leukemia (CLL), are prevalent throughout the world, and are a leading cause of cancer associated mortalities.[1] The treatment of B cell malignancies have advanced significantly with the use of immunotherapies.[2] CD20, a B cell specific transmembrane protein encoded for by the MS4A1 gene, has received particular attention as an immunotherapy target since the late 1980's, and monoclonal antibodies (mAbs) targeting CD20 are commonly applied in combination regimens.[3-5] The clinical importance of anti-CD20 mAbs is highlighted by the addition of Rituximab, the first FDA approved of anti-CD20 mAb, to the WHOs list of essential medicines.

Despite the success of anti-CD20 mAbs, the overall response rates to CD20 targeted immunotherapy for the treatment of B cell malignancies remains unsatisfactory.[6,7] The efficacy of these antibodies is largely limited by the degree to which CD20 is expressed, and this is dependent upon the type of B cell malignancy.[8,9] For example, CLL malignant cells express low levels of CD20 compared to other B cell malignancies, therefore CLL patients respond poorly to anti-CD20 mAbs.[10-12] Furthermore, acquired resistance to anti-CD20 mAbs, due to decreased CD20 expression, and additional factors that inhibit the therapeutic mechanisms associated with these antibodies, are prevalent in relapsing patients irrespective of the specific malignancy.[13-19] As such, efforts to pharmacologically modulate CD20 expression are of great interest.

To date, efforts to modulate CD20 expression pharmacologically both at transcriptional and posttranscriptional levels have been the focus of much investigation. The promise of this approach is highlighted in cases that demonstrate that increasing CD20 expression can sensitize cells to the action of anti-CD20 mAbs. These approaches have focused on the modulation of pathways that have been well characterized to impact CD20 expression. However, there is still need for approaches and compounds that increase CD20 expression in B cell malignancies so as to sensitize such cells to the action of anti-CD20 mAbs.

Thus, in an aspect, the present technology provides a compound according to Formula I

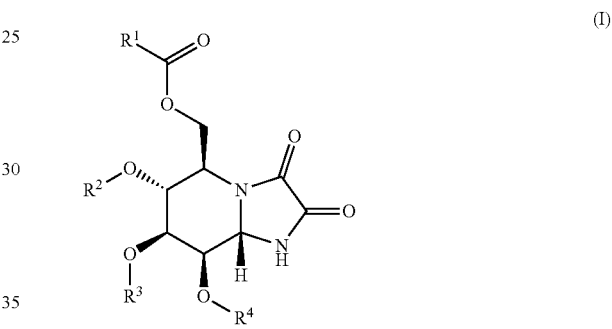

(I)

or a pharmaceutically acceptable salt and/or solvate thereof, where $R^1$ is an unsubstituted $C_1$-$C_{12}$ alkyl; and $R^2$, $R^3$, and $R^4$ are each independently H or —C(O)-(unsubstituted $C_1$-$C_{12}$ alkyl). For ease of reference, the compounds included in any aspect or embodiment herein may be referred to anywhere in this disclosure as "a compound of the present technology," "compounds of the present technology," or the like. The compounds of the present technology are also referred to herein as "kifunensine derivatives," "kifunensine analogs," and the like. Similarly for ease of reference, the compositions, medicaments, and pharmaceutical compositions of the present technology may collectively be referred to herein as "compositions," "compositions of the present technology," or the like. The present disclosure demonstrates that the expression of CD20 is altered upon the inhibition of type I α-mannosidase enzymes. The ability of these enzymes to modulate CD20 expression has not been previously described. Type I α-mannosidase enzymes play an important role in N-glycosylation, and while CD20 is not N-glycosylated, and is thus not directly affected by the action of these enzymes, the present disclosure evidences that the significant upregulation of CD20 by the inhibition of α-mannosidase enzymes by compounds of the present technology potentiates the activity of anti-CD20 mAbs and importantly sensitize cell lines that are resistant to the action of these antibodies.

In any embodiment herein, it may be that $R^1$ is an unsubstituted $C_1$-$C_6$ alkyl. In any embodiment herein, it may be that $R^2$, $R^3$, and $R^4$ are each independently H or —C(O)-(unsubstituted $C_1$-$C_6$ alkyl). In any embodiment herein, it may be that $R^1$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$. In any embodiment herein, it may be that $R^2$, $R^3$, and $R^4$ are each independently H, —C(O)CH_3, —C(O)CH_2CH_3, —C(O)CH_2CH_2CH_3, —C(O)CH(CH_3)_2, —C(O)CH_2CH_2CH_2CH_3, —C(O)CH_2CH(CH_3)_2, —C(O)CH_2CH_2CH_2CH_2CH_3, or —C(O)CH_2CH_2CH(CH_3)_2.

In any embodiment herein, it may be that the compound is of Formula Ia

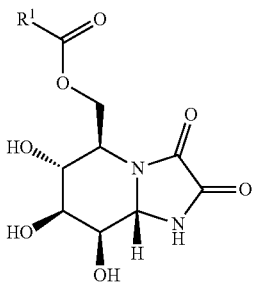

(Ia)

or a pharmaceutically acceptable salt and/or solvate thereof;
of Formula Ib

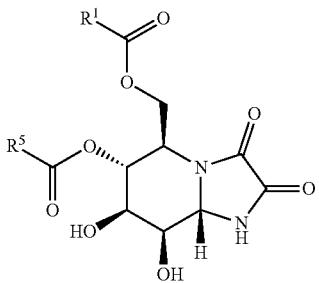

(Ib)

or a pharmaceutically acceptable salt and/or solvate thereof;
of Formula Ic

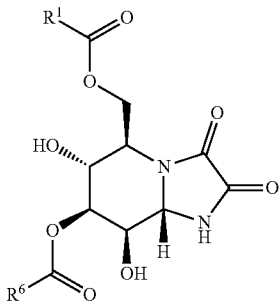

(Ic)

or a pharmaceutically acceptable salt and/or solvate thereof;
of Formula Id

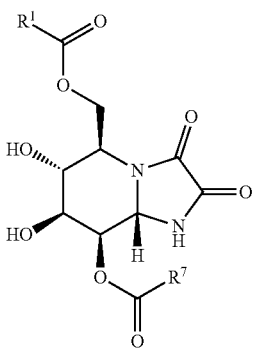

(Id)

or a pharmaceutically acceptable salt and/or solvate thereof;
of Formula Ie

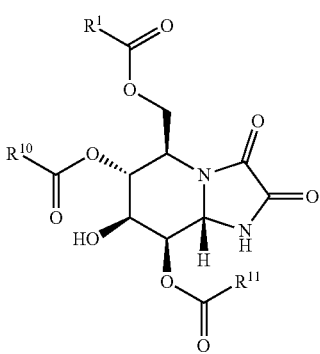

(Ie)

or a pharmaceutically acceptable salt and/or solvate thereof;
of Formula If (If)

or a pharmaceutically acceptable salt and/or solvate thereof; or of Formula Ig

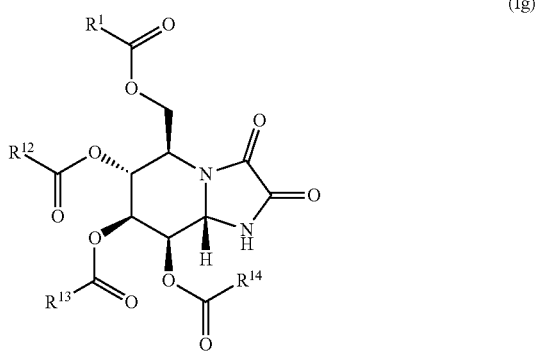

(Ig)

or a pharmaceutically acceptable salt and/or solvate thereof; where $R^5$, $R^6$, $R^7$, $R^8$, $R^9$, $R^{10}$, $R^{11}$, $R^{12}$, $R^{13}$, and $R^{14}$ are each independently an unsubstituted $C_1$-$C_{12}$ alkyl. In any embodiment herein, it may be that $R^5$, $R^6$, $R^7$, $R^8$, $R^9$, $R^{10}$, $R^{11}$, $R^{12}$, $R^{13}$, and $R^{14}$ are each independently an unsubstituted $C_1$-$C_6$ alkyl. In any embodiment herein, it may be that $R^5$, $R^6$, $R^7$, $R^8$, $R^9$, $R^{10}$, $R^{11}$, $R^{12}$, $R^{13}$, and $R^{14}$ are each independently $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

In any embodiment herein, it may be that the compound is of Formula Ib and each of $R^1$ and $R^5$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

In any embodiment herein, it may be that the compound is of Formula Ic and each of $R^1$ and $R^6$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

In any embodiment herein, it may be that the compound is of Formula Id and each of $R^1$ and $R^7$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

In any embodiment herein, it may be that the compound is of Formula Ie and each of $R^1$, $R^8$, and $R^9$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

In any embodiment herein, it may be that the compound is of Formula If and each of $R^1$, $R^{10}$, and $R^{11}$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

In any embodiment herein, it may be that the compound is of Formula Ig and each of $R^1$, $R^{12}$, $R^{13}$, and $R^{14}$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

In an aspect, a composition is provided that includes a compound of any embodiment disclosed herein, a pharmaceutically acceptable carrier or one or more excipients, fillers or agents (collectively referred to hereafter as "pharmaceutically acceptable carrier" unless otherwise indicated and/or specified). In a related aspect, a medicament for treating a B-cell malignancy in a subject is provided that includes a compound of any embodiment disclosed herein and optionally a pharmaceutically acceptable carrier. The medicament of any embodiment herein may include an effective amount of the compound for treating the B-cell malignancy when combined with an anti-CD20 monoclonal antibody, such as an anti-CD20 monoclonal antibody as disclosed in Payandeh, Z. et al. "The applications of anti-CD20 antibodies to treat various B cells disorders," *Biomedicine & Pharmacotherapy* 2019, 109, 2415-2426. Thus, in any embodiment herein, the anti-CD20 monoclonal antibody may include one or more of rituximab, Y90-ibritumomab, tositumomab, reditux, veltuzumab, ocaratuzumab, PRO131921, ublituzimab, TRU-015, ofatumumab, obinutuzumab, and ocrelizumab. In any embodiment herein, the B-cell malignancy may be non-Hodgkin lymphoma or chronic lymphocytic leukemia. In a related aspect, a pharmaceutical composition is provided that includes (i) an effective amount of a compound of any embodiment disclosed herein, wherein the effective amount of the compound is effective to treat a B-cell malignancy; and (ii) a pharmaceutically acceptable carrier. In any embodiment herein, the B-cell malignancy may be non-Hodgkin lymphoma or chronic lymphocytic leukemia. In a related aspect, a pharmaceutical composition is provided that includes (i) an effective amount of a compound of any embodiment disclosed herein, where the compound is present in an amount effective to treat a B-cell malignancy when combined with an anti-CD20 monoclonal antibody; and (ii) a pharmaceutically acceptable carrier. In any embodiment herein, the anti-CD20 monoclonal antibody may include one or more of rituximab, Y90-ibritumomab, tositumomab, reditux, veltuzumab, ocaratuzumab, PRO131921, ublituzimab, TRU-015, ofatumumab, obinutuzumab, and ocrelizumab. In any embodiment herein, the B-cell malignancy may be non-Hodgkin lymphoma or chronic lymphocytic leukemia. In further related aspects, the present technology provides methods including a compound of any aspect or embodiment disclosed herein and/or a composition of any embodiment disclosed herein and/or a medicament of any embodiment disclosed herein.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, reduction of a tumor mass. In any aspect or embodiment disclosed herein (collectively referred to herein as "any embodiment herein," "any embodiment disclosed herein," or the like) of the compositions, pharmaceutical compositions, and methods including compounds of the present technology, the effective amount may be an amount effective in treating a B-cell malignancy (such as non-Hodgkin lymphoma or chronic lymphocytic leukemia), treating a tumor, and/or shrinking a tumor. By way of example, the effective amount of any embodiment herein including a compound of the present technology may be from about 0.01 μg to about 200 mg of the compound (such as from about 0.1 μg to about 50 mg of the compound or about 10 μg to about 20 mg of the compound). The methods and uses according to the present technology may include an effective amount of a compound of any embodiment disclosed herein. In any aspect or embodiment disclosed herein, the effective amount may be determined in relation to a subject. As used herein, a "subject" or "patient" is a mammal, such as a cat, dog, rodent or primate. Typically the subject is a human, and, preferably, a human suffering from or suspected of suffering from pain. The term "subject" and "patient" can be used interchangeably.

Thus, the instant present technology provides pharmaceutical compositions and medicaments including a compound of any embodiment disclosed herein (or a composition of any embodiment disclosed herein) and a pharmaceutically acceptable carrier. The compositions may be used in the methods and treatments described herein. The pharmaceutical composition may be packaged in unit dosage form. The unit dosage form may be effective in treating a B-cell malignancy (such as non-Hodgkin lymphoma or chronic lymphocytic leukemia). The unit dosage form may be effective in treating a tumor by reducing a tumor volume when administered to a subject in need thereof. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1\times10^{-4}$ g/kg to 1 g/kg, preferably, $1\times10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to parenteral solutions, oral solutions, powders, tablets, pills, gelcaps, capsules, lozenges, suppositories, patches, nasal sprays, injectables, implantable sustained-release formulations, mucoadherent films, topical varnishes, lipid complexes, liquids, etc.

The pharmaceutical compositions and medicaments may be prepared by mixing one or more compounds and/or compositions of the present technology with pharmaceutically acceptable carriers, excipients, binders, diluents or the like. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars and/or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until, for example, there is a reduction in the mass of a tumor in a subject. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the B-cell malignancy (e.g., non-Hodgkin lymphoma or chronic lymphocytic leukemia) associated with the tumor, and the pharmacological activity of the compound being used. The determination of optimum dosages for a particular patient is well known to those skilled in the art.

Various assays and model systems can be readily employed to determine the therapeutic effectiveness of the treatment according to the present technology. Effectiveness of the compositions (as well as determination of effective amounts) and methods of the present technology may also be demonstrated by a decrease in the mass of a tumor and/or slowing the growth of a tumor and/or affecting an increase in the therapeutic responsiveness of a B-cell malignancy to an anti-CD20 monoclonal antibody.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

The compounds of the present technology can also be administered to a patient along with other conventional therapeutic agents that may be useful in the treatment of tumors or in vaccination. The administration may include oral administration, parenteral administration, or nasal administration. In any of these embodiments, the administration may include intratumoral injections, subcutaneous injections, intravenous injections, intraperitoneal injections, or intramuscular injections. In any of these embodiments, the administration may include oral administration. The methods of the present technology can also include administering, either sequentially or in combination with one or more compounds of the present technology, a conventional therapeutic agent in an amount that can potentially or synergistically be effective for the treatment a B-cell malignancy (e.g., non-Hodgkin lymphoma or chronic lymphocytic leukemia).

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1 \times 10^{-4}$ g/kg to 1 g/kg, preferably, $1 \times 10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest. Suitable labels are known by those skilled in the art and can include, for example, radioisotopes, radionuclides, isotopes, fluorescent groups, biotin (in conjunction with streptavidin complexation), and chemiluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic—hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

As indicated previously in this disclosure, in an aspect a method of treating a subject suffering from a B-cell malignancy is provided, where the method includes administering to the subject an effective amount of a compound of any embodiment disclosed herein or administering an effective amount of a composition of any embodiment disclosed herein, and an effective amount of an anti-CD20 monoclonal antibody. In any embodiment herein of the method, the administering may include intratumoral administration. In any embodiment herein, the B-cell malignancy may be non-Hodgkin lymphoma or chronic lymphocytic leukemia.

In an aspect, a method of treating cancer arising from a B-cell malignancy in a subject is provided, where the method includes administering to the subject an effective amount of a compound of any embodiment disclosed herein or administering an effective amount of a composition of any embodiment disclosed herein, and optionally an effective amount of an anti-CD20 monoclonal antibody. In any embodiment herein of the method, the administering may include intratumoral administration. In any embodiment herein, the B-cell malignancy may be non-Hodgkin lymphoma or chronic lymphocytic leukemia.

In any embodiment herein, the administering may further include administration of a chemotherapeutic agent such as an alkylating agent; a nitrosourea; an antimetabolite; an anthracycline; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a vinca alkaloid; a microtubule poison, or a combination of any two or more thereof. In any embodiment herein, the administering may further include administration of a chemotherapeutic agent such as busulfan, cisplatin, carboplatin, oxaliplatin, an octahedral platinum (IV) compound, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, vinblastine, vincristine, vinorelbine, prednisone, dexamethasone, L-asparaginase, dactinomycin, thalidomide, tretinoin, imatinib (Gleevec), gefitinib (Iressa), erlotinib (Tarceva), rituximab (Rituxan), bevacizumab (Avastin), ipilimumab, nivolumab (Opdivo), pembrolizumab (Ketruda), tamoxifen, fulvestrant, anastrozole, exemestane, letrozole, megestrol acetate, bicalutamide, flutamide, leuprolide, goserelin, or a combination of any two or more thereof.

In any embodiment herein, the administering may include local administration of the compound to a site in the subject including the cancer or local administration of the composition to a site in the subject including the cancer. In any embodiment herein, the administering may include oral, rectal, nasal, vaginal, transdermal, intravenous, intramuscular, or inhalation administration. In any embodiment herein, the administering may include injection of the compound into the site in the subject including the cancer or proximal to the site in the subject including the cancer.

In any embodiment herein, the administering may further include administration of a chemotherapeutic agent such as an alkylating agent; a nitrosourea; an antimetabolite; an anthracycline; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a vinca alkaloid; a microtubule poison, or a combination of any two or more thereof. In any embodiment herein, the administering may further include administration of a chemotherapeutic agent such as busulfan, cisplatin, carboplatin, oxaliplatin, an octahedral platinum (IV) compound, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, vinblastine, vincristine, vinorelbine, prednisone, dexamethasone, L-asparaginase, dactinomycin, thalidomide, tretinoin, imatinib (Gleevec), gefitinib (Iressa), erlotinib (Tarceva), rituximab (Rituxan), bevacizumab (Avastin), ipilimumab, nivolumab (Opdivo), pembrolizumab (Ketruda), tamoxifen, fulvestrant, anastrozole, exemestane, letrozole, megestrol acetate, bicalutamide, flutamide, leuprolide, goserelin, or a combination of any two or more thereof.

In any embodiment herein, the administering may include local administration of the compound to the tumor or local administration of the composition to the tumor. In any embodiment herein, the administering may include oral, rectal, nasal, vaginal, transdermal, intravenous, intramuscular, or inhalation administration. In any embodiment herein, the administering may include injection of the compound into the tumor or proximal to the tumor.

In an aspect, the present technology provides a method of producing high mannose glycoproteins, where such a method may include contacting a cell culture with a compound of any embodiment disclosed herein thus generating the high mannose glycoproteins. In any embodiment herein, the cell culture may include malignant B-cells such as non-Hodgkin lymphoma cells, chronic lymphocytic leukemia cells, diffuse large B cell lymphoma cells, Burkitt lymphoma cells, follicular lymphoma cells, or a combination of any two or more thereof. In any embodiment herein, the cell culture may include Raji cells, rituximab resistant cells, or both. The high mannose glycoproteins may include high mannose N-glycans on the surface of malignant B-cells. In any embodiment herein, the cell culture may include Raji cells, rituximab resistant cells, or both.

The examples herein are provided to illustrate advantages of the present technology and to further assist a person of ordinary skill in the art with preparing or using the compounds and compositions of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects, or embodiments of the present technology.

EXAMPLES

Reagents and cell lines. Rituximab was purchased from Roche. Obinutuzumab and ofatumumab were purchased from Evidentic. Kifunensine was prepared as described in the art.

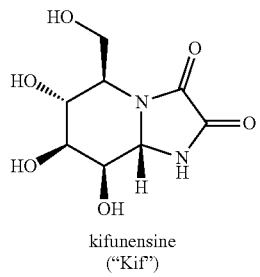

kifunensine
("Kif")

1-deoxymannojirimycin hydrochlorie (DMJ), swainsonine (Swain), 1,4-dideoxy-1,4-imino-D-mannitol (DIM), cycloheximide (Cyclo) and actinomycin D (Act D) were purchased from Cayman Chemical Company. Cell lines were purchased from ATCC and DSMZ. Rituximab resistant cell lines Raji 2R, Raji 4RH and RL 4RH were developed as previously described.[20,21] Cell lines derived from malignant B cells were maintained in RPMI 1640 medium with HEPES 5 mmol/L, sodium pyruvate 1 mmol/L, 1% NEAA (GIBCO), 10% premium heat-inactivated FBs (Corning), and 100 μg/mL Normicin (Invivogen) at 37° C. in a fully humidified atmosphere of 5% $CO_2$. CD16+NK-92 cells (PTA-6967, ATCC) were maintained in X-VIVO 10 (Lonza) containing 5% heat-inactivated human serum, type AB (MP Biomedicals), 100 IU/mL IL-2 (R&D Systems) and 100 μg/mL Normicin at 37° C. in a fully humidified atmosphere of 5% $CO_2$. Pooled human AB serum used in CDC assays was purchased from Innovative Research.

Staining of surface antigens. Cells were treated for 48 hours with the described inhibitors at the indicated concentrations or with DMSO controls. Cells were then harvested, washed twice with cold flow buffer (PBS (GIBCO) containing 0.5% BSA and 0.1% sodium azide (Fisher)), stained for 1 hour with 0.25 μg of anti-CD20 mAb (clone 2H7) conjugated with Super Bright 645 (eBioscience, ThermoFisher Scientific), then washed twice with flow buffer, and finally the cells were incubated with flow buffer containing 2.5 μg/mL 7-aminoactinomycin (7-AAD, eBioscience, ThermoFisher Scientific) for 10 minutes prior to being analyzed using an Attune NxT Flow Cytometer. CD20 expression was assessed in 7-AAD negative cells.

ADCC assays. Target cells were labelled with CellTrace Violet according to the manufacturer's instructions (ThermoFisher Scientific). In brief, 1 million target cells were washed twice with warm PBS, then stained with 5 μM CellTrace Violet in PBS for 20 minutes at 37° C. Then, 5 volume equivalents of complete media were added and the resulting solution was incubated for 10 minutes at 37° C. The cells were pelleted and washed twice with fresh complete media, and the cell suspension was adjusted to 800,000 cells/mL in complete media. 25 μL of the target cell suspension (i.e., 20,000 target cells) were then in added to a 96-well plate. 25 μL of rituximab solutions at 4× the indicated concentrations in complete media or complete media were added to experiment wells and the control wells respectively, and the resulting suspensions were incubated for 30 minutes at 37° C. Subsequently, 50 μL of a 1.6 million CD-16+ NK-92 cells/mL suspension in complete media (E:T 4:1, i.e., 80,000 effector cells) were added to experiment wells and control wells (i.e., no antibody) and the plate was incubated for 4 hours at 37° C. in a fully humidified atmosphere of 5% $CO_2$. Subsequently, 6 uL of 2.5 μg/mL was added to each well and after 10 minutes the plate was analyzed using an Attune NxT Flow Cytometer. Target cell viability was accessed by determining the percentage of CellTrace Violet and 7-AAD positive cells. ADCC was calculated as follows: % ADCC=% 7-AAD positive target cells in experiment well—% 7-AAD positive target cells in control wells.

CDC assays. 25 μL of the target cell suspension at 2 million cells/mL (i.e., 50,000 target cells) were added to a 96-well plate. 25 μL of antibody solutions at 4× the indicated concentrations in complete media or complete media were added to experiment wells and the control wells respectively, and the resulting suspensions were incubated for 30 minutes at 37° C. Subsequently, 50 μL of a 20% of pooled human serum in complete media were added to experiment wells and control wells (i.e., no antibody) and the plate was incubated for 1 hours at 37° C. in a fully humidified atmosphere of 5% $CO_2$. Subsequently, 6 uL of 2.5 μg/mL was added to each well and after 10 minutes the plate was analyzed using an Attune NxT Flow Cytometer. Target cell viability was accessed by determining the percentage of 7-AAD positive cells. CDC was calculated as follows: % CDC=% 7-AAD positive target cells in experiment well—% 7-AAD positive target cells in control wells.

Synthesis of Kifunensine Analogues 10a-c

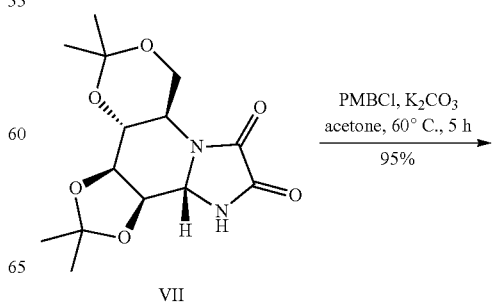

VII

VIII (SK-II-131)

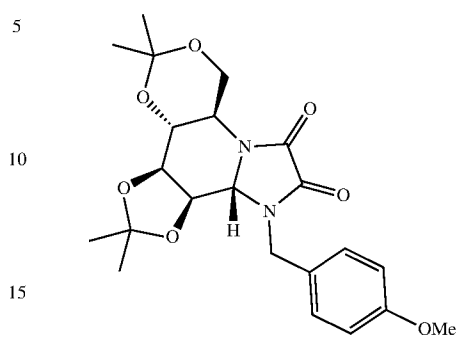

To a solution of 2,3:4,6-di-O-isopropylidene kifunensine[3] (VII, 800 mg, 2.561 mmol, 1 equiv.) in anhydrous acetone (20 mL), powdered K$_2$CO$_3$ (700 mg, 5.102 mmol, 1.5 equiv.), tetrabutylammonium iodide (39 mg, 0.256, 0.1 equiv.) and PMBCl (510 µL, 3.823 mmol, 1.5 equiv.) were added. The reaction mixture was heated to 60° C. for 5 hours and then cooled to room temperature, inorganics were removed by filtration and the organic layer was concentrated under reduced pressure. The resulting residue was diluted with cold water (20 mL) and was extracted with EtOAc (3×25 mL). The organic phase was washed with brine (25 mL), dried over Na$_2$SO$_4$, filtered and concentrated under reduced pressure. The crude residue was then purified by CombiFlash using EtOAc in Hexanes (1:1) to yield pure VIII (1.05 g, 95%) as a white solid.

$^1$H NMR (400 MHz, CDCl$_3$): δ7.30 (d, J=8.00 Hz, 2H), 6.88 (d, J=8.00 Hz, 2H), 5.23 (dd, J=14.50 Hz, J=2.40 Hz, 1H), 4.66 (ddd, J=10.90 Hz, J=4.80 Hz, J=1.80 Hz, 1H), 4.57 (d, J=8.50 Hz, 1H), 4.41-4.29 (m, 2H), 4.16 (td, J=8.30, J=2.00 Hz, 1H), 4.08 (dd, J=11.2, J=8.30 Hz, 1H), 3.81 (s, 3H), 3.69 (t, J=10.60 Hz, 1H), 3.57 (td, J=10.7, J=4.70 Hz, 1H), 1.61 (s, 3H), 1.51 (s, 3H), 1.47 (s, 3H), 1.41 (s, 3H)

$^{13}$C NMR (101 MHz, CDCl$_3$): δ159.7, 159.6, 130.6, 127.4, 114.2, 112.1, 100.1, 78.3, 75.9, 70.6, 66.4, 61.6, 55.4, 47.8, 44.7, 29.1, 26.6, 24.2, 19.1

HRMS (ESI) calcd for [M+H]$^+$ C$_{22}$H$_{29}$N$_2$O$_7$ 433.1975, Found 433.1973

FTIR (thin film): 1754, 1721, 1514, 1244, 1038 cm$^{-1}$ $$[\alpha]_D^{25} = +87° \ (c = 0.023 \text{ g/mL, MeOH})$$

IX (SK-II-139)

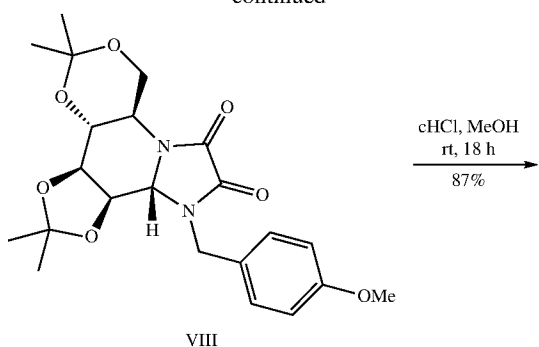

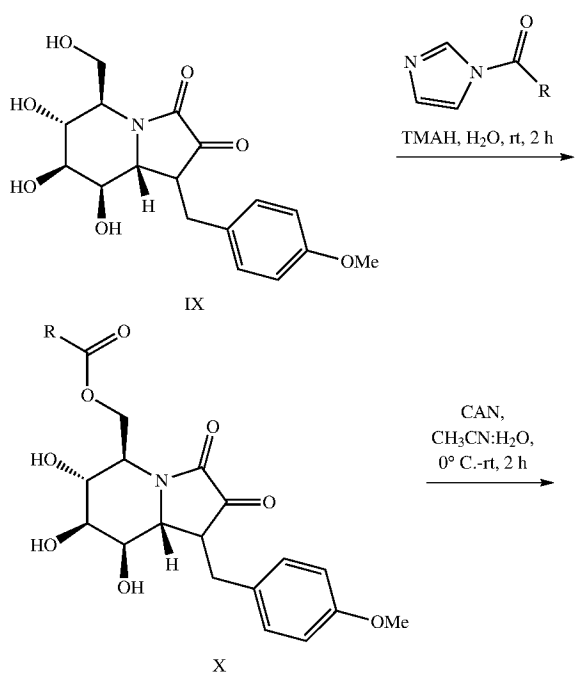

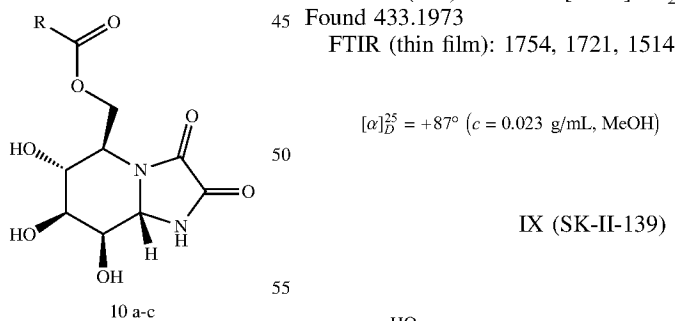

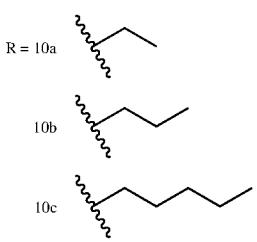

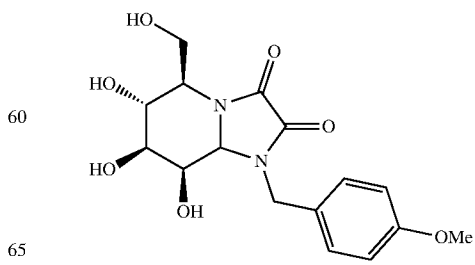

VIII (1.0 g, 2.312 mmol, 1 equiv.) was dissolved in MeOH (5 mL) and cooled to approximately 5° C. Concentrated HCl (2 mL) was added dropwise over 5 minutes and the mixture was stirred at ambient temperature for 18 hrs. Volatiles were removed by evaporation under reduced pressure, and the crude residue was then purified by CombiFlash using MeOH in DCM (9:1) to yield pure IX (710 mg, 87%) as an off-white solid.

$^1$H NMR (400 MHz, CD$_3$OD): δ7.33 (d, J=8.00 Hz, 2H), 6.89 (d, J=8.00 Hz, 2H), 5.13 (d, J=14.50 Hz, 1H), 4.87 (d, J=8.90 Hz, 1H), 4.78 (d, J=14.60 Hz, 1H), 4.40 (dd, J=8.80 Hz, J=4.70 Hz, 1H), 4.01 (dd, J=3.70 Hz, 1.20 Hz, 1H), 3.92 (t, J=3.30 Hz, 1H), 3.86 (dd, J=11.90 Hz, J=8.80 Hz, 1H), 3.78 (s, 3H), 3.75 (d, J=3.10 Hz, 1H), 3.67 (dd, J=12.00 Hz, J=4.80 Hz, 1H)

$^{13}$C NMR (101 MHz, CD$_3$OD): δ160.8, 160.4, 160.2, 131.0, 129.3, 115.1, 73.6, 73.5, 70.2, 66.9, 61.7, 60.0, 55.7, 46.5

HRMS (ESI) calcd for [M+H]$^+$ C$_{16}$H$_{21}$N$_2$O$_7$ 353.1349, Found 353.1342

FTIR (thin film): 3315, 1667,1515,1275,1024

$$[\alpha]_D^{25} = +291° \ (c = 0.0010 \text{ g/mL, MeOH})$$

General Procedure for Regioselective acetylation of N-PMB-Kifunensine: N-PMB-kifunensine (IX, 1 equiv.) was dissolved in water (1 mL/15 mg of IX) and dissolved by heating at 60° C., and then allowed to cool room temperature. Tetramethyl-ammonium hydroxide (TMAH) (25% aq. 1.3 equiv.) was added, followed by the desired N-acyl imidazole derivatives[4] (3.0 equiv.) in two portions. The resulting reaction mixture was stirred at room temperature for another 2-3 hours. Reaction mixture was diluted with acetonitrile, and directly purified by reverse phase HPLC to afford acetylated products

Xa (SK-IV-044)

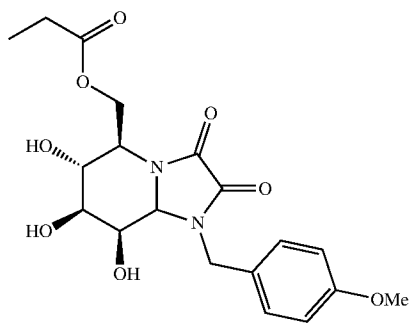 [SMILES: CCC(=O)OC[C@@H]1[C@@H](O)[C@H](O)[C@H](O)C2N(Cc3ccc(OC)cc3)C(=O)C(=O)N21]

Yield: 43%

$^1$H NMR (500 MHz, MeOD) δ7.31 (d, J=8.70 Hz, 2H), 6.92 (d, J=8.60 Hz, 2H), 5.15 (d, J=14.70 Hz, 1H), 4.99 (d, J=9.0 Hz, 1H), 4.82-4.70 (m, 2H), 4.54 (dd, J=10.70 Hz, J=3.70 Hz, 1H), 4.14 (dd, J=11.80 Hz, J=3.80 Hz, 1H), 4.03 (dd, J=3.70 Hz, J=1.20 Hz, 1H), 3.96 (t, J=3.40 Hz, 1H), 3.81 (s, 3H), 3.79 (d, merged in singlet, J=3.0 Hz, 1H), 2.27 (q, J=7.60 Hz, 2H), 1.05 (t, J=7.50 Hz, 3H)

$^{13}$C NMR (126 MHz, MeOD) δ174.3, 159.5, 158.7, 158.6, 129.3, 127.8, 113.7, 72.1, 72.0, 68.6, 65.3, 61.4, 55.9, 54.3, 45.3, 26.7, 7.9

HRMS (ESI) calcd for [M+Na]$^+$ C$_{19}$H$_{24}$N$_2$O$_8$Na 431.1430, found 431.1423

FTIR (thin film): 3360, 1734, 1514,1248

$$[\alpha]_D^{25} = +82° \ (c = 0.002 \text{ g/mL, MeOH})$$

Xb (SK-IV-046)

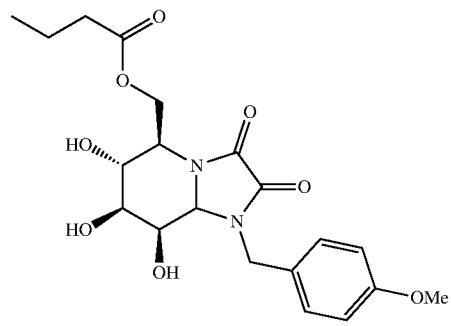 [SMILES: CCCC(=O)OC[C@@H]1[C@@H](O)[C@H](O)[C@H](O)C2N(Cc3ccc(OC)cc3)C(=O)C(=O)N21]

Yield: 38%

$^1$H NMR (400 MHz, MeOD) δ7.31 (d, J=8.60 Hz, 2H), 6.92 (d, J=8.70 Hz, 2H), 5.15 (d, J=14.60 Hz, 1H), 4.99 (d, J=9.0 Hz, 1H), 4.82-4.75 (m, 2H), 4.55 (dd, J=10.70 Hz, J=3.60 Hz, 1H), 4.10 (dd, J=11.80 Hz, J=3.70 Hz, 1H), 4.03 (dd, J=3.80 Hz, J=1.30 Hz, 1H), 3.96 (t, J=3.30 Hz, 1H), 3.81 (s, 3H), 3.79 (dd, merged in singlet, J=3.0 Hz, 1H), 2.23 (t, J=7.30 Hz, 2H), 1.54 (h, J=7.40 Hz, 2H), 0.87 (t, J=7.40 Hz, 3H)

$^{13}$C NMR (101 MHz, MeOD) δ174.9, 160.9, 160.2, 160.1, 130.8, 129.2, 115.1, 73.6, 73.5, 66.7, 62.7, 57.3, 55.7, 46.7, 36.7, 19.3, 14.0

HRMS (ESI) calcd for [M+Na]$^+$ C$_{20}$H$_{26}$N$_2$O$_8$Na 445.1587, found 445.1575

FTIR (thin film): 3374, 1728, 1642, 1513, 1216, 1057

$$[\alpha]_D^{25} = +41° \ (c = 0.001 \text{ g/mL, MeOH})$$

Xc (SK-IV-052)

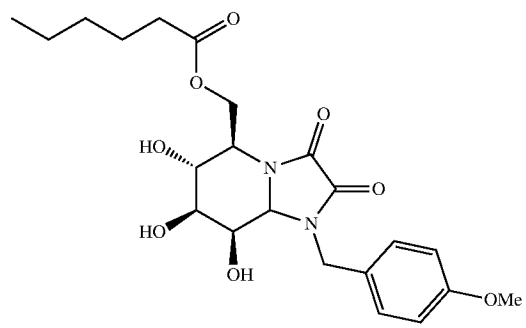 [SMILES: CCCCCC(=O)OC[C@@H]1[C@@H](O)[C@H](O)[C@H](O)C2N(Cc3ccc(OC)cc3)C(=O)C(=O)N21]

Yield: 35%

$^1$H NMR (400 MHz, MeOD) δ6.82 (d, J=8.30 Hz, 2H), 6.40 (d, J=8.30 Hz, 2H), 4.65 (d, J=14.70 Hz, 1H), 4.50 (d,

J=8.90 Hz, 1H), 4.35-4.25 (m, 2H), 4.05 (dd, J=10.70 Hz, J=3.70 Hz, 1H), 3.60 (dd, J=11.90 Hz, J=3.70 Hz, 1H), 3.53 (d, J=3.60 Hz, 1H), 3.46 (t, J=3.40 Hz, 1H), 3.31 (s, 3H), 3.27-3.30 (m, merged in singlet, 1H), 1.75 (t, J=7.40 Hz, 2H), 1.03 (p, J=7.40 Hz, 2H), 0.89-0.69 (m, 4H), 0.41 (t, J=7.0 Hz, 3H)

$^{13}$C NMR (101 MHz, MeOD) δ175.0, 160.9, 160.0, 160.1, 130.7, 129.2, 115.1, 73.6, 73.5, 66.7, 62.7, 57.3, 55.7, 46.7, 34.7, 32.3, 25.5, 23.4, 14.2

HRMS (ESI) calcd for [M+Na]$^+$ C$_{22}$H$_{30}$N$_2$O$_8$Na 473.1900, found 473.1909

FTIR (thin film): 3368, 1728, 1612, 1513, 1216, 1098

$[\alpha]_D^{25} = +65°$ (c = 0.001 g/mL, MeOH)

SK-IV-048

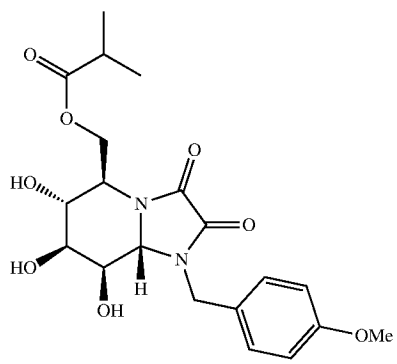

IVc

This reaction was stirred at 45° C. for 24 h and then purified; starting material was recovered.

Yield: 31%

$^1$H NMR (500 MHz, MeOD) δ7.31 (d, J=8.40 Hz, 2H), 6.92 (d, J=8.60 Hz, 2H), 5.16 (d, J=14.70 Hz, 1H), 4.99 (d, J=8.90 Hz, 1H), 4.84 (t, J=11.40 Hz, 1H), 4.78 (d, J=14.70 Hz, 1H), 4.56 (dd, J=11.0 Hz, J=3.80 Hz, 1H), 4.08 (dd, J=11.90 Hz, J=3.90 Hz, 1H), 4.02 (d, J=3.70 Hz, 1H), 3.96 (t, J=3.40 Hz, 1H), 3.81 (s, 3H), 3.79 (dd, J=9.0 Hz, J=3.0 Hz, 1H), 2.47 (quin., J=7.0 Hz, 1H), 1.08 (d, J=7.0 Hz, 3H), 1.05 (d, J=7.0 Hz, 3H)

$^{13}$C NMR (126 MHz, MeOD) δ178.2, 160.9, 160.2, 160.0, 130.7, 129.2, 115.1, 73.7, 73.5, 70.0, 66.6, 62.4, 57.2, 55.7, 46.7, 35.0, 19.3, 19.2

HRMS (ESI) calcd for [M+H]$^+$ C$_{20}$H$_{27}$N$_2$O$_8$ 423.1767, found 423.1743

$[\alpha]_D^{25} = +30.8°$ (c = 0.002 g/mL, MeOH)

SK-IV-050

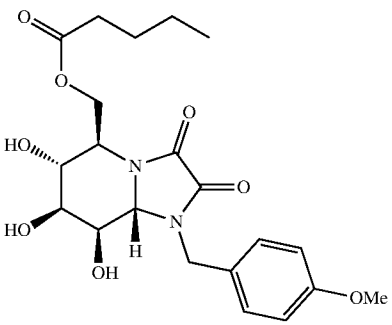

IVe

Yield: 50%

$^1$H NMR (400 MHz, MeOD) δ7.32 (d, J=8.80 Hz, 2H), 6.91 (d, J=8.70 Hz, 2H), 5.15 (d, J=14.70 Hz, 1H), 5.01 (d, J=9.0 Hz, 1H), 4.84-4.73 (m, 2H), 4.55 (dd, J=10.70 Hz, J=3.70 Hz, 1H), 4.10 (dd, J=11.80 Hz, J=3.70 Hz, 1H), 4.04 (dd, J=3.90 Hz, J=1.30 Hz, 1H), 3.97 (t, J=3.40 Hz, 1H), 3.80 (s, 3H), 3.78-3.83 (dd, merged in singlet, 1H), 2.25 (t, J=7.40 Hz, 2H), 1.54-1.45 (m, 2H), 1.34-1.21 (m, 2H), 0.90 (t, J=7.40 Hz, 3H)

$^{13}$C NMR (101 MHz, MeOD) δ175.0, 160.8, 160.2, 160.1, 130.7, 129.1, 115.1, 73.6, 73.5, 66.7, 62.6, 57.2, 55.7, 46.7, 34.4, 28.0, 23.1, 14.0

HRMS (ESI) calcd for [M+Na]$^+$ C$_{21}$H$_{28}$N$_2$O$_8$Na 459.1743, found 459.1706

$[\alpha]_D^{25} = +78.3°$ (c = 0.00115 g/mL, MeOH)

General Procedure of PMB deprotection: CAN (3 equiv.) in water was added dropwise to an ice-cold solution of Xa-c (1 equiv.) in acetonitrile (1:1 ratio of acetonitrile to water was used) over a period of 15 minutes. Then, the reaction mixture was warmed to ambient temperature, and stirred for another 1.5 hrs. The reaction mixture was concentrated under reduced pressure to remove acetonitrile and the reaction solution was extracted with EtOAc (3×), washed with brine and dried over Na$_2$SO$_4$, filtered and the resulting solution was concentrated under reduced pressure. The crude residue was purified by reverse phase HPLC followed by lyophilization to obtain desired 6-O-acylated kifunensine analogs 10a-c.

10a (SK-IV-045)

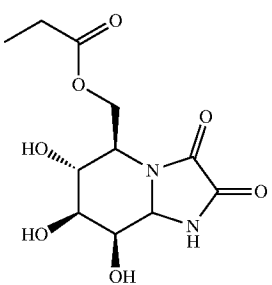 [SMILES: CCC(=O)OC[C@@H]1[C@@H](O)[C@H](O)[C@H](O)C2NC(=O)C(=O)N21]

Yield: 80%

¹H NMR (500 MHz, MeOD) δ5.02 (d, J=9.10 Hz, 1H), 4.77 (dd, J=11.80 Hz, J=10.6 Hz, 1H), 4.44 (dd, J=10.60 Hz, J=3.80 Hz, 1H), 4.21 (dd, J=11.80, J=3.80 Hz, 1H), 4.05 (dd, J=3.80 Hz, J=1.10 Hz, 1H), 3.98 (d, J=3.30 Hz, 1H), 3.54 (dd, J=9.10 Hz, J=2.80 Hz, 1H), 2.34 (q, J=7.50 Hz, 2H), 1.11 (t, J=7.5 Hz, 3H)

¹³C NMR (126 MHz, MeOD) δ175.9, 161.6, 160.2, 73.0, 73.1, 70.6, 64.6, 63.0, 57.3, 28.2, 9.3

HRMS (ESI) calcd for [M+Na]⁺ $C_{11}H_{16}N_2O_7Na$ 311.0855, found 311.0853

FTIR (thin film): 3375, 1728, 1642, 1513, 1216, 1057

$[\alpha]_D^{25} = -82°$ (c = 0.001 g/mL, MeOH)

SK-IV-049

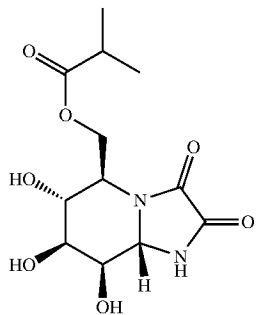

Vc

Yield: 75%

¹H NMR (500 MHz, MeOD) δ5.06 (d, J=9.0 Hz, 1H), 4.84 (t, J=11.30 Hz, 1H), 4.51 (dd, J=10.70 Hz, J=3.80 Hz, 1H), 4.20 (dd, J=11.90 Hz, 3.90 Hz, 1H), 4.07 (d, J=3.80 Hz, 1H), 3.99 (t, J=3.40 Hz, 1H), 3.57 (dd, J=9.10, J=2.80 Hz, 1H), 2.29 (t, J=7.30 Hz, 2H), 1.62 (h, J=7.30 Hz, 2H), 0.94 (t, J=7.40 Hz, 3H)

¹³C NMR (126 MHz, MeOD) δ175.1, 161.9, 160.5, 73.1, 73.1, 70.6, 64.5, 62.9, 57.3, 36.7, 19.2, 13.9

HRMS (ESI) calcd for [M+Na]⁺ $C_{12}H_{18}N_2O_7Na$ 325.1012, found 325.0989

FTIR (thin film): 3374, 1730, 1642, 1513, 1057

$[\alpha]_D^{25} = +21°$ (c = 0.001, MeOH)

SK-IV-051

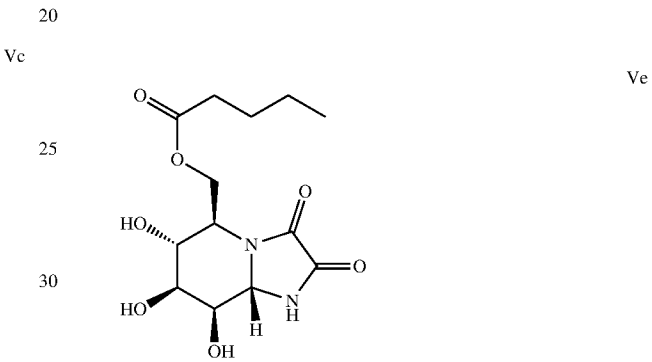

Ve

Yield: 84%

¹H NMR (500 MHz, MeOD) δ5.06 (d, J=9.10 Hz, 1H), 4.85 (dd, J=11.80 Hz, J=10.7 Hz, 1H), 4.51 (dd, J=10.80 Hz, J=3.80 Hz, 1H), 4.19 (dd, J=11.8 Hz, J=3.80 Hz, 1H), 4.07 (dd, J=3.80 Hz, J=1.20 Hz, 1H), 4.00 (d, J=3.2 Hz, 1H), 3.57 (dd, J=9.0 Hz, J=2.80 Hz, 1H), 2.54 (quin., J=7.0 Hz, 1H), 1.13 (t, J=7.4 Hz, 6H)

¹³C NMR (126 MHz, MeOD) δ178.5, 161.8, 160.4, 73.2, 73.1, 70.7, 64.5, 62.9, 57.3, 35.1, 19.3, 19.2

HRMS (ESI) calcd for [M+H]⁺ $C_{12}H_{19}N_2O_7$ 303.1192, found 303.1212

$[\alpha]_D^{25} = -8°$ (c = 0.001, MeOH)

10b (SK-IV-047)

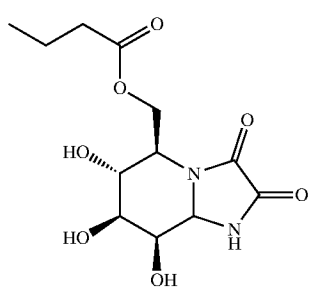 [SMILES: CCCC(=O)OC[C@@H]1[C@@H](O)[C@H](O)[C@H](O)C2NC(=O)C(=O)N21]

Yield: 69%

¹H NMR (500 MHz, MeOD) δ5.05 (d, J=9.10 Hz, 1H), 4.84 (t, J=11.30 Hz, 1H), 4.51 (dd, J=10.80 Hz, J=3.80 Hz, 1H), 4.20 (dd, J=11.80 Hz, J=3.80 Hz, 1H), 4.07 (d, J=3.60 Hz, 1H), 3.99 (t, J=3.30 Hz, 1H), 3.57 (dd, J=9.10 Hz, J=2.80 Hz, 1H), 2.32 (t, J=7.40 Hz, 2H), 1.57 (p, J=7.40 Hz, 2H), 1.34 (h, J=7.40 Hz, 2H), 0.93 (t, J=7.40 Hz, 3H)

¹³C NMR (126 MHz, MeOD) δ175.2, 161.8, 160.5, 73.1, 73.1, 70.6, 64.5, 62.9, 57.2, 34.6, 27.9, 23.2, 14.0

HRMS (ESI) calcd for [M+Na]⁺ $C_{13}H_{20}N_2O_7Na$ 339.1168, found 339.1146

$[\alpha]_D^{25} = +25°$ (c = 0.001, MeOH)

10c (SK-IV-053)

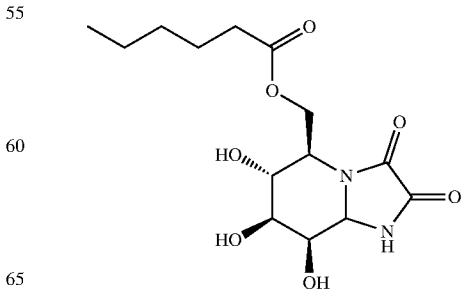

Yield: 71%

$^1$H NMR (500 MHz, MeOD) δ5.05 (d, J=9.0 Hz, 1H), 4.84 (dd, J=11.9 Hz, J=10.70 Hz, 1H), 4.51 (dd, J=10.7 Hz, J=3.80 Hz, 1H), 4.19 (dd, J=11.9 Hz, J=3.80 Hz, 1H), 4.07 (dd, J=3.80 Hz, J=1.30 Hz, 1H), 3.99 (t, J=3.30 Hz, 1H), 3.57 (dd, J=9.10 Hz, J=2.90 Hz, 1H), 2.31 (t, J=7.40 Hz, 2H), 1.59 (hept, J=6.60 Hz, 2H), 1.40-1.24 (m, 4H), 0.93 (t, J=7.10 Hz, 3H)

$^{13}$C NMR (126 MHz, MeOD) δ175.2, 161.8, 160.5, 73.2, 73.1, 70.6, 64.5, 62.9, 57.2, 34.8, 32.3, 25.5, 23.3, 14.2

HRMS (ESI) calcd for [M+H]$^+$ C$_{14}$H$_{23}$N$_2$O$_7$ 331.1505, found 331.1514

FTIR (thin film): 3376, 1728, 1641, 1513, 1057

$[\alpha]_D^{25} = +5°(c = 0.001, \text{MeOH})$

General Procedure for Acylation of XI

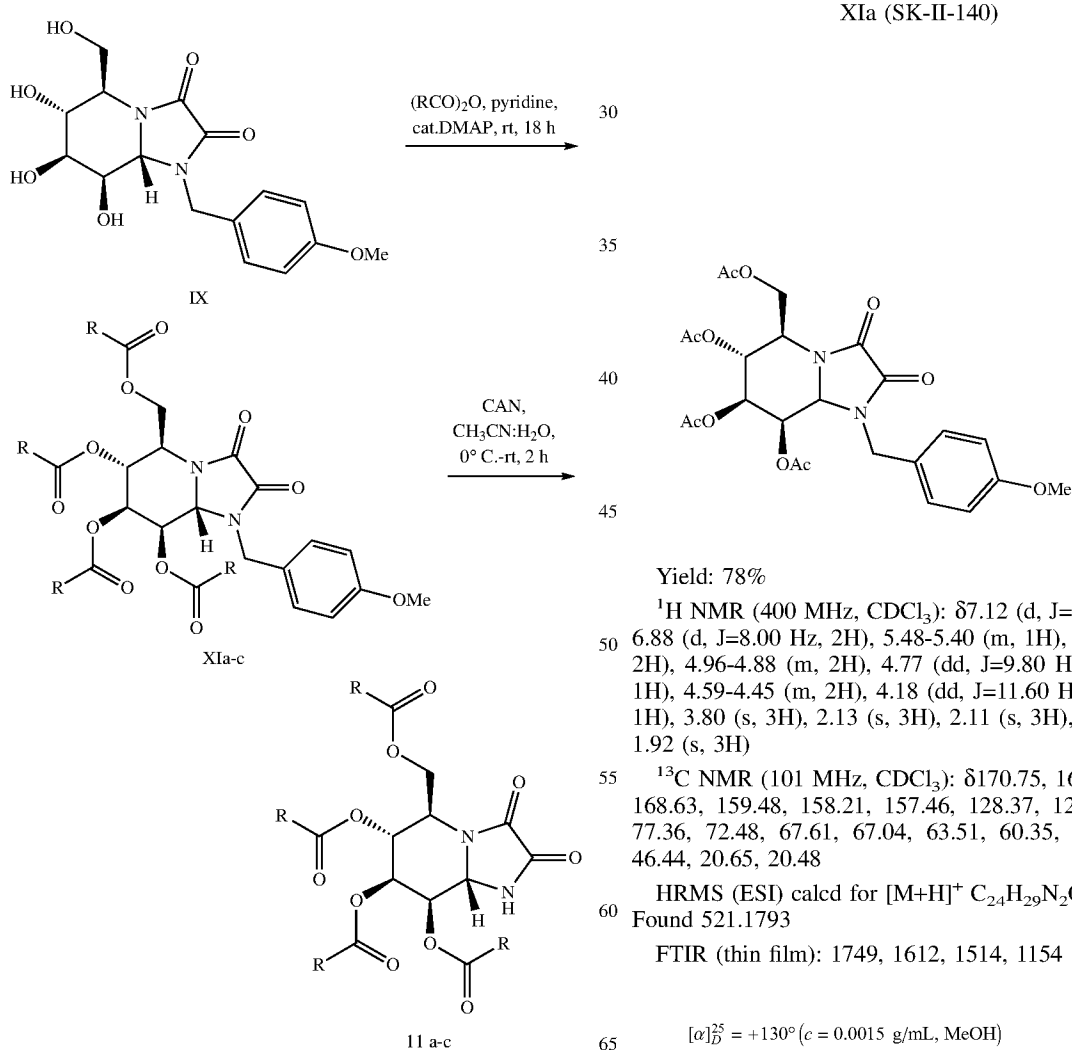

To an ice-cold solution of IX (1 equiv.) in anhydrous pyridine (excess), acetic, propionic, or butanoic anhydride (10 equiv.), and DMAP (0.1 equiv.) were added. The reaction mixture was stirred for 18 hrs. Volatiles were removed by evaporation, and the resulting residue was diluted with water, extracted with EtOAc (3 times), washed with 1N HCl, brine and dried over Na$_2$SO$_4$, filtered and the solution was evaporated under reduced pressure. The crude product obtained was purified by CombiFlash using EtOAc in Hexanes to yield desired XIa-c.

XIa (SK-II-140)

Yield: 78%

$^1$H NMR (400 MHz, CDCl$_3$): δ7.12 (d, J=8.00 Hz, 2H), 6.88 (d, J=8.00 Hz, 2H), 5.48-5.40 (m, 1H), 5.11-5.04 (m, 2H), 4.96-4.88 (m, 2H), 4.77 (dd, J=9.80 Hz, J=5.20 Hz, 1H), 4.59-4.45 (m, 2H), 4.18 (dd, J=11.60 Hz, J=5.20 Hz, 1H), 3.80 (s, 3H), 2.13 (s, 3H), 2.11 (s, 3H), 2.03 (s, 3H), 1.92 (s, 3H)

$^{13}$C NMR (101 MHz, CDCl$_3$): δ170.75, 169.03, 168.64, 168.63, 159.48, 158.21, 157.46, 128.37, 126.90, 114.43, 77.36, 72.48, 67.61, 67.04, 63.51, 60.35, 55.32, 52.42, 46.44, 20.65, 20.48

HRMS (ESI) calcd for [M+H]$^+$ C$_{24}$H$_{29}$N$_2$O$_{11}$ 521.1771, Found 521.1793

FTIR (thin film): 1749, 1612, 1514, 1154

$[\alpha]_D^{25} = +130°(c = 0.0015 \text{ g/mL, MeOH})$

XIb (JDW-I-112)

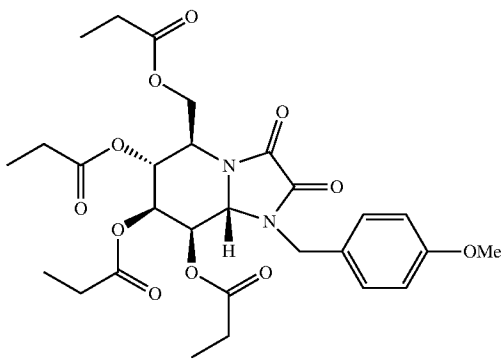 [SMILES: CCC(=O)OC[C@@H]1[C@@H](OC(=O)CC)[C@H](OC(=O)CC)[C@H](OC(=O)CC)[C@H]2N(Cc3ccc(OC)cc3)C(=O)C(=O)N12]

Yield: 81%

¹H NMR (400 MHz, CDCl₃) δ7.12 (d, J=8.60 Hz, 2H), 6.87 (d, J=8.80 Hz, 2H), 5.48-5.45 (m, 1H), 5.09-5.04 (m, 2H), 5.01 (d, J=15.20 Hz, 1H), 4.93 (dd, J=9.3 Hz, J=3.0 Hz, 1H), 4.75 (dd, J=10.0 Hz, J=5.10 Hz, 1H), 4.61 (dd, J=11.4 Hz, J=10.0 Hz, 1H), 4.40 (d, J=15.10 Hz, 1H), 4.12 (dd, J=11.4 Hz, J=5.2 Hz, 1H), 3.80 (s, 3H), 2.37 (qd, J=7.50 Hz, J=2.0 Hz, 4H), 2.29 (q, J=7.5 Hz, 2H), 2.23-2.13 (m, 2H), 1.14 (t, J=7.60 Hz, 6H), 1.06 (t, J=7.60 Hz, 6H)

¹³C NMR (101 MHz, CDCl₃): δ174.2, 172.5, 172.2, 159.6, 158.0, 157.4, 128.7, 126.9, 114.5, 72.9, 67.1, 66.9, 63.2, 60.1, 55.4, 52.6, 46.4, 27.5, 27.4, 27.3, 27.2, 9.2, 9.0, 8.9, 8.5

HRMS (ESI) calcd for [M+Na]⁺ C₂₈H₃₆N₂O₁₁Na 599.2217, found 599.2239

FTIR (thin film): 1748, 1616, 1514, 1154

$[\alpha]_D^{25} = +8.8°\ (c = 0.003\ g/mL,\ CHCl_3)$

JDW-I-117

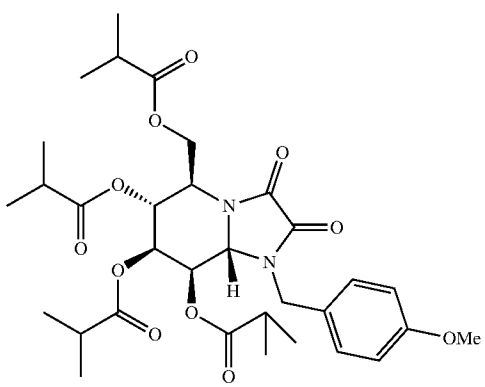 [SMILES: COc1ccc(CN2C(=O)C(=O)N3[C@H](COC(=O)C(C)C)[C@@H](OC(=O)C(C)C)[C@H](OC(=O)C(C)C)[C@H](OC(=O)C(C)C)[C@@H]23)cc1]

Color: off-white foam
Yield: 78%

¹H NMR (400 MHz, CDCl₃) δ7.15 (d, J=8.80 Hz, 2H), 6.87 (d, J=8.60 Hz, 2H), 5.51 (t, J=3.3 Hz, 1H), 5.22 (d, J=14.90 Hz, 1H), 5.09 (d, J=9.30 Hz, 1H), 5.03 (d, J=3.90 Hz, 1H), 4.97 (dd, J=9.30 Hz, J=2.90 Hz, 1H), 4.79-4.66 (m, 2H), 4.21 (d, J=14.90 Hz, 1H), 4.05-3.98 (m, 1H), 3.80 (s, 3H), 2.64-4.53 (m, 2H), 2.48 (quin., J=14.10 Hz, 2H), 1.27-1.11 (m, 18H), 1.06 (dd, J=11.0 Hz, J=7.0 Hz, 6H)

¹³C NMR (101 MHz, CDCl₃) δ176.7, 175.0, 174.8, 174.5, 159.7, 157.8, 157.3, 129.0, 126.6, 114.5, 73.7, 67.0, 66.8, 62.4, 59.6, 55.3, 52.4, 46.0, 34.0, 33.0, 33.7, 33.7, 19.1, 18.9, 18.7, 18.7, 18.5

HRMS (ESI) calcd for [M+Na]⁺ C₃₂H₄₄N₂O₁₁Na 655.2843, found 655.2817

$[\alpha]_D^{25} = +18.2°\ (c = 0.004\ g/mL,\ CHCl_3)$

XIc JDW-I-114

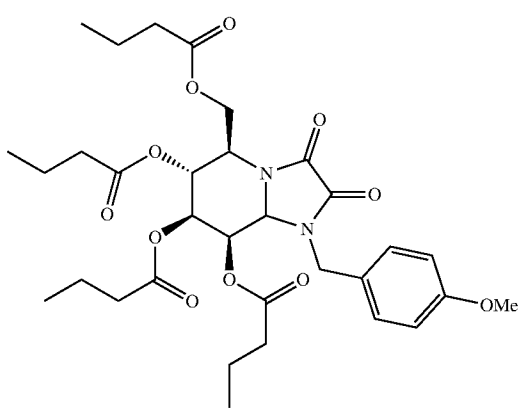 [SMILES: CCCC(=O)OC[C@@H]1[C@@H](OC(=O)CCC)[C@H](OC(=O)CCC)[C@H](OC(=O)CCC)C2N(Cc3ccc(OC)cc3)C(=O)C(=O)N21]

Yield: 78%

¹H NMR (400 MHz, CDCl₃) δ7.13 (d, J=8.60 Hz, 2H), 6.87 (d, J=8.70 Hz, 2H), 5.48 (t, J=3.40 Hz, 1H), 5.15-5.02 (m, 3H), 4.95 (dd, J=9.3 Hz, J=3.0 Hz, 1H), 4.75 (dd, J=10.0 Hz, J=5.20 Hz, 1H), 4.60 (dd, J=11.40 Hz, J=10.0 Hz, 1H), 4.32 (d, J=15.10 Hz, 1H), 4.10 (dd, J=11.4 Hz, J=5.20 Hz, 1H), 3.81 (s, 3H), 2.33 (t, J=7.40 Hz, 4H), 2.25 (t, J=7.40 Hz, 2H), 2.22-2.05 (m, 2H), 1.50-1.78 (m, 8H), 1.01-0.83 (m, 12H)

¹³C NMR (101 MHz, CDCl₃) δ173.3, 171.6, 171.3, 171.2, 159.6, 157.9, 157.3, 126.7, 114.4, 72.9, 67.0, 66.9, 62.9, 60.0, 55.3, 52.5, 46.2, 35.9, 35.8, 35.7, 35.5, 18.5, 18.2, 18.1, 17.7, 13.6, 13.6, 13.5

HRMS (ESI) calcd for [M+Na]⁺ C₃₂H₄₄N₂O₁₁Na 655.2843, found 655.2880

FTIR (thin film): 1749, 1616, 1514

$[\alpha]_D^{25} = +17.33°\ (c = 0.003\ g/mL,\ CHCl_3)$

JDW-I-115

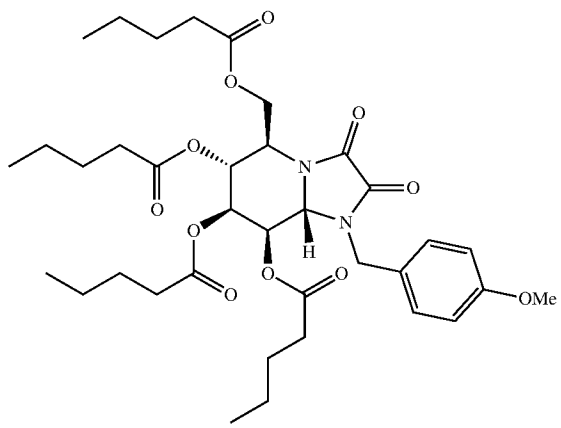
IVe

Color: Thick liquid
Yield: 78%
¹H NMR (400 MHz, CDCl₃) δ7.12 (d, J=8.60 Hz, 2H), 6.87 (d, J=8.60 Hz, 2H), 5.47 (t, J=3.40 Hz, 1H), 5.14-5.01 (m, 3H), 4.94 (dd, J=9.30 Hz, J=3.0 Hz, 1H), 4.74 (dd, J=10.0 Hz, J=5.10 Hz, 1H), 4.61 (dd, J=11.40 Hz, 9.90 Hz, 1H), 4.35 (d, J=15.10 Hz, 1H), 4.09 (dd, J=11.40 Hz, J=5.20 Hz, 1H), 3.80 (s, 3H), 2.42-2.33 (t, J=7.20 Hz, 4H), 2.27 (t, J=7.5 Hz, 2H), 2.23-2.00 (m, 2H), 1.66-1.44 (m, 8H), 1.41-1.19 (m, 8H), 0.84-0.96 (m, 12H)
¹³C NMR (101 MHz, CDCl₃) δ173.5, 171.9, 171.5, 171.5, 159.6, 158.0, 157.3, 128.7, 126.8, 114.4, 72.9, 67.1, 66.9, 63.0, 60.0, 55.3, 52.5, 46.3, 33.7, 33.6, 33.6, 33.5, 27.0, 26.7, 26.7, 26.4, 13.7, 13.7, 13.7, 13.6
HRMS (ESI) calcd for [M+Na]⁺ C₃₆H₅₂N₂O₁₁Na 711.3469, found 711.3419

$[\alpha]_D^{25} = +15.7°\ (c = 0.0042\ \text{g/mL, CHCl}_3)$

JDW-I-118

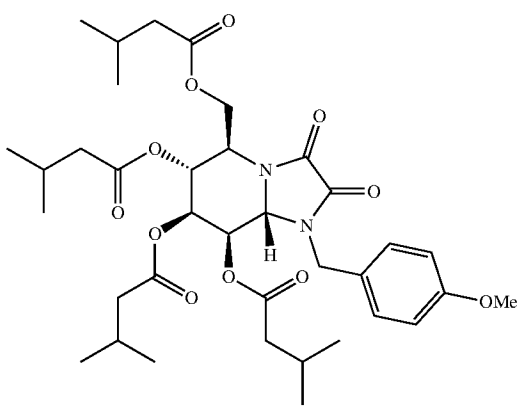
IVf

Color: Thick liquid
Yield: 78%
¹H NMR (400 MHz, CDCl₃) δ7.13 (d, J=8.70 Hz, 2H), 6.88 (d, J=8.70 Hz, 2H), 5.48 (t, J=3.30 Hz, 1H), 5.17 (d, J=14.90 Hz, 1H), 5.08-5.00 (m, 2H), 4.97 (dd, J=9.30 Hz, J=2.80 Hz, 1H), 4.75 (dd, J=9.9 Hz, J=5.30 Hz, 1H), 4.58 (dd, J=11.50 Hz, J=9.80 Hz, 1H), 4.25 (d, J=15.10 Hz, 1H), 4.09 (dd, J=11.5 Hz, J=5.40 Hz, 1H), 3.81 (s, 3H), 2.32-2.19 (m, 4H), 2.18-1.91 (m, 8H), 0.92-1.0 (m, 18H), 0.88 (d, J=6.6 Hz, 6H)
¹³C NMR (101 MHz, CDCl₃) δ172.7, 171.1, 170.8, 159.6, 157.9, 157.3, 129.0, 126.7, 114.5, 73.0, 67.2, 66.9, 62.7, 60.0, 55.3, 52.5, 46.1, 43.1, 42.8, 42.8, 42.6, 25.9, 25.6, 25.4, 25.1, 22.5, 22.4, 22.4, 22.3, 22.3
HRMS (ESI) calcd for [M+Na]⁺ C₃₆H₅₂N₂O₁₁Na 711.3469, found 711.3454

$[\alpha]_D^{25} = +13.5°\ (c = 0.004\ \text{g/mL, CHCl}_3)$

JDW-I-116

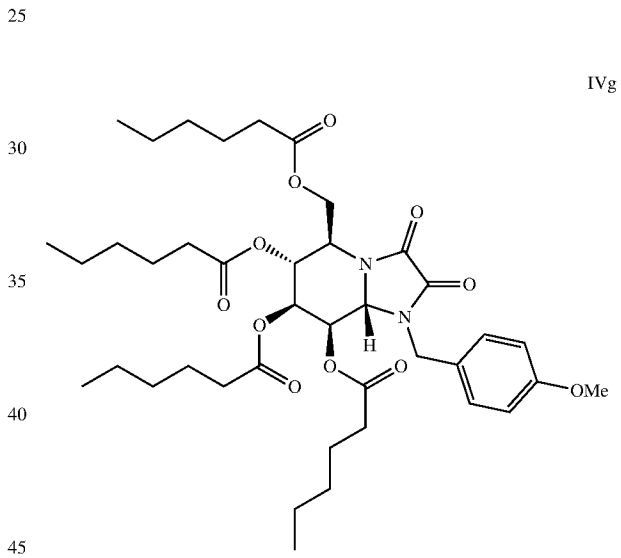
IVg

Color: Thick syrup
Yield: 78%
¹H NMR (400 MHz, CDCl₃) δ7.12 (d, J=8.70 Hz, 2H), 6.87 (d, J=8.70 Hz, 2H), 5.47 (t, J=3.40 Hz, 1H), 5.10-5.00 (m, 3H), 4.94 (dd, J=9.30 Hz, J=3.0 Hz, 1H), 4.75 (dd, J=9.90 Hz, J=5.20 Hz, 1H), 4.60 (dd, J=11.4 Hz, J=9.90 Hz, 1H), 4.37 (d, J=15.1 Hz, 1H), 4.10 (dd, J=11.50 Hz, J=5.20 Hz, 1H), 3.80 (s, 3H), 2.41-2.30 (m, 4H), 2.30-2.01 (m, 4H), 1.69-1.49 (m, 12H), 1.36-1.18 (m, 12H), 0.99-0.77 (m, 12H)
¹³C NMR (101 MHz, CDCl₃) δ173.5, 171.5, 171.4, 159.6, 158.0, 157.3, 128.6, 126.8, 114.4, 72.9, 67.1, 66.9, 63.1, 60.0, 55.3, 52.5, 46.3, 34.0, 33.9, 33.8, 33.7, 31.2, 31.2, 31.1, 31.1, 24.6, 24.4, 24.3, 24.0, 22.3, 22.3, 22.3, 22.2, 13.9
HRMS (ESI) calcd for [M+Na]⁺ C₄₀H₆₀N₂O₁₁Na 767.4095, found 767.4080

$[\alpha]_D^{25} = +25.7°\ (c = 0.004\ \text{g/mL, CHCl}_3)$

General Procedure of PMB deprotection. A solution of CAN (3 equiv.) in water was added dropwise to an ice-cold solution of XIa-c (1 equiv.) in acetonitrile (1:1 ratio of acetonitrile-water used) over a period of 15 minutes. The resulting reaction mixture was warmed to ambient temperature and stirred for another 1.5 hours. Reaction mixture was then concentrated under reduced pressure and residue obtained was diluted with water and extracted with EtOAc (3×), washed with brine, dried over $Na_2SO_4$, filtered and the resulting solution was concentrated under reduced pressure. The crude residue was purified by CombiFlash using EtOAc in Hexanes to obtain desired 11a-c.

11a (SK-II-141)

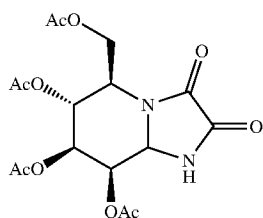 [SMILES: CC(=O)OC[C@@H]1[C@@H](OC(C)=O)[C@H](OC(C)=O)[C@H](OC(C)=O)C2NC(=O)C(=O)N21]

Yield: 73%

$^1$H NMR (500 MHz, $CDCl_3$) δ9.62 (s, 1H), 5.42 (t, J=3.30 Hz, 1H), 5.21 (d, J=9.30 Hz, 1H), 5.08 (d, J=3.60 Hz, 1H), 5.00 (dd, J=9.00 Hz, J=3.00 Hz, 1H), 4.70 (dd, J=9.90 Hz, J=4.70 Hz, 1H), 4.61 (t, J=10.70 Hz, 1H), 4.23 (dd, J=11.50 Hz, J=4.90 Hz, 1H), 2.19 (s, 3H), 2.11 (s, 3H), 2.10 (s, 3H), 2.05 (s, 3H)

$^{13}$C NMR (123.7 MHz, $CDCl_3$): δ170.9, 169.7, 169.2, 168.7, 160.8, 157.6, 71.3, 67.6, 67.5, 61.0, 60.3, 52.7, 20.8, 20.8, 20.7, 20.6

HRMS (ESI) calcd for $[M+H]^+$ $C_{16}H_{21}N_2O_{10}$ 401.1196, Found 401.1176

FTIR (thin film): 1848, 1741, 1533, 1050

$[\alpha]_D^{25} = +25.2° (c = 0.00115$ g/mL, MeOH$)$ 11b (JDW-II-004)

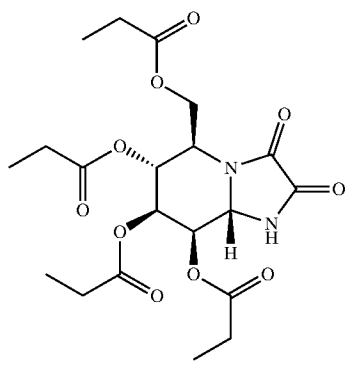 [SMILES: CCC(=O)OC[C@@H]1[C@@H](OC(=O)CC)[C@H](OC(=O)CC)[C@H](OC(=O)CC)[C@H]2NC(=O)C(=O)N12]

Yield: 75%

$^1$H NMR (400 MHz, $CDCl_3$) δ9.08 (s, 1H), 5.49 (t, J=3.40 Hz, 1H), 5.24 (d, J=9.50 Hz, 1H), 5.11 (d, J=3.70 Hz, 1H), 4.92 (dd, J=9.50 Hz, J=3.0 Hz, 1H), 4.74-4.64 (m, 2H), 4.25-4.14 (m, 1H), 2.66-2.16 (m, 8H), 1.21 (t, J=7.60 Hz, 3H), 1.16-0.82 (m, 9H)

$^{13}$C NMR (101 MHz, $CDCl_3$) δ174.4, 173.0, 172.6, 172.2, 160.6, 157.6, 71.5, 67.3, 61.0, 52.8, 27.5, 27.3, 27.2, 9.1, 8.8, 8.7

HRMS (ESI) calcd for $[M+Na]^+$ $C_{20}H_{28}N_2O_{10}Na$ 479.1642, Found 479.1649

FTIR (thin film): 1738, 1462, 1151, 1093

$[\alpha]_D^{25} = -16° (c = 0.002$ g/mL, $CHCl_3)$

JDW-II-006

Vc

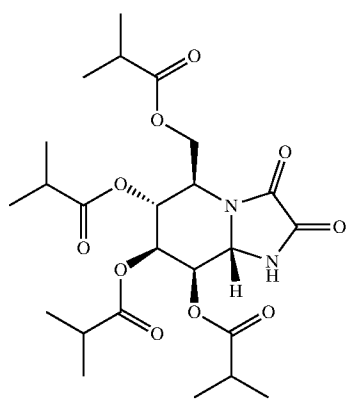

Color: White solid

Yield: 73%

$^1$NMR (400 MHz, $CDCl_3$) δ5.51 (t, J=3.40 Hz, 1H), 5.27 (d, J=9.40 Hz, 1H), 5.09 (dd, J=3.70, 1.10 Hz, 1H), 4.90-4.90 (m, 2H), 4.71 (dd, J=10.5 Hz, J=4.70 Hz, 1H), 4.11 (dd, J=11.10 Hz, J=4.60 Hz, 1H), 2.75-2.49 (m, 4H), 1.34-1.11 (m, 24H)

$^{13}$C NMR (101 MHz, $CDCl_3$) δ177.1, 175.5, 175.1, 174.7, 160.5, 157.3, 72.1, 67.2, 67.0, 61.0, 60.0, 52.7, 34.1, 33.8, 19.2, 19.0, 18.9, 18.7, 18.6

HRMS (ESI) calcd for $[M+Na]^+$ $C_{24}H_{36}N_2O_{10}Na$ 535.2268, found 535.2302

$[\alpha]_D^{25} = -36.6° (c = 0.0026$ g/mL, $CHCl_3)$ 11c (JDW-II-010)

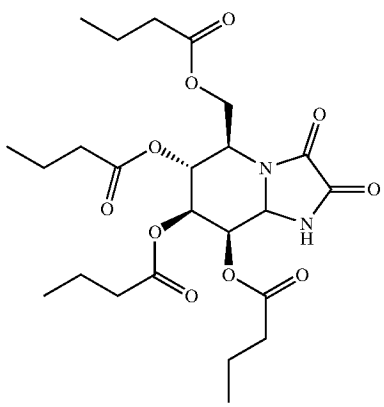 [SMILES: CCCC(=O)OC[C@@H]1[C@@H](OC(=O)CCC)[C@H](OC(=O)CCC)[C@H](OC(=O)CCC)C2NC(=O)C(=O)N21]

Yield: 73%
$^1$H NMR (400 MHz, CDCl$_3$) δ9.36 (s, 1H), 5.48 (t, J=3.40 Hz, 1H), 5.22 (d, J=9.40 Hz, 1H), 5.09 (d, J=3.70 Hz, 1H), 4.91 (dd, J=9.4 Hz, J=3.0 Hz, 1H), 4.74-4.65 (m, 2H), 4.17 (q, J=6.3 Hz, 1H), 2.45-2.24 (m, 8H), 1.79-1.53 (m, 8H), 1.11-0.83 (m, 12H)
$^{13}$C NMR (126 MHz, CDCl$_3$) δ173.6, 172.2, 171.8, 171.3, 71.7, 67.3, 67.2, 60.9, 60.1, 52.8, 36.0, 35.9, 35.8, 35.7, 18.1, 18.3, 18.3, 13.7, 13.7, 13.6
HRMS (ESI) calcd for [M+Na]$^+$ C$_{24}$H$_{36}$N$_2$O$_{10}$Na 535.2268, found 535.2251
FTIR (thin film): 1747, 1418, 1153, 1050

$[α]_D^{25} = -16.7°\ (c = 0.0028\ \text{g/mL, CHCl}_3)$

JDW-II-002

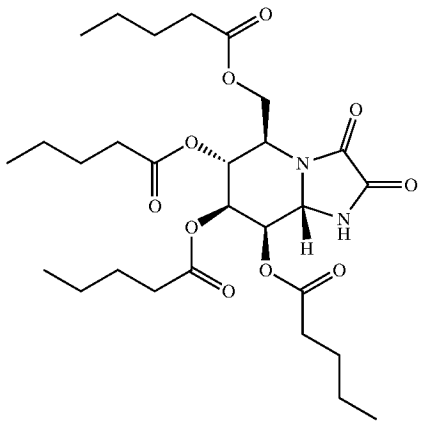

Ve

Color: White solid
Yield: 73%
$^1$H NMR (400 MHz, CDCl$_3$) δ8.87 (s, 1H), 5.49 (t, J=3.30 Hz, 1H), 5.23 (d, J=9.40 Hz, 1H), 5.09 (d, J=3.60 Hz, 1H), 4.89 (dd, J=9.3 Hz, J=3.0 Hz, 1H), 4.79-4.65 (m, 2H), 4.15 (dd, J=9.50 Hz, J=2.80 Hz, 1H), 2.46-2.24 (m, 8H), 1.77-1.49 (m, 8H), 1.44-1.25 (m, 8H), 1.03-0.80 (m, 12H)
$^{13}$C NMR (101 MHz, CDCl$_3$) δ173.8, 172.4, 172.0, 171.5, 160.7, 157.4, 71.6, 67.3, 67.2, 61.0, 60.2, 52.8, 33.8, 33.6, 33.6, 33.5, 26.9, 26.8, 26.7, 26.6, 22.2, 22.2, 22.2, 13.7, 13.7, 13.6
HRMS (ESI) calcd for [M+Na]$^+$ C$_{28}$H$_{44}$N$_2$O$_{10}$Na 591.2894, found 591.2857

JDW-II-005

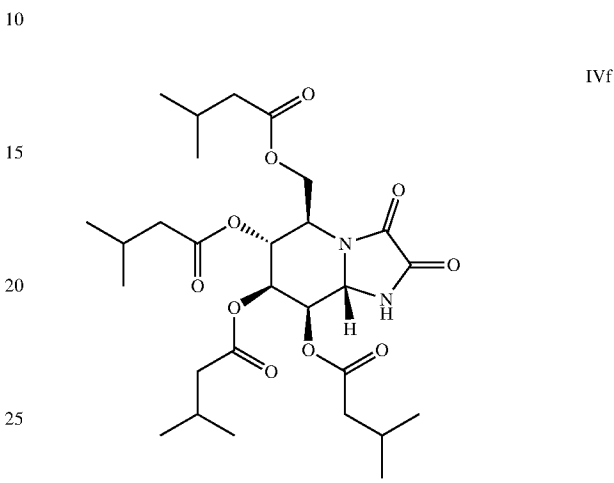

IVf

Color: White solid
Yield: 73%
$^1$H NMR (400 MHz, CDCl$_3$) δ8.67 (s, 1H), 5.50 (t, J=3.30 Hz, 1H), 5.24 (d, J=9.40 Hz, 1H), 5.11-5.06 (m, 1H), 4.89 (dd, J=9.40, J=3.0 Hz, 1H), 4.80-4.64 (m, 2H), 4.14 (dd, J=10.0 Hz, J=3.60 Hz, 1H), 2.38-1.97 (m, 12H), 1.01 (d, J=6.70 Hz, 6H), 0.95 (dd, J=6.80 Hz, J=1.60 Hz, 12H), 0.92 (dd, J=6.70 Hz, J=1.0 Hz, 6H)
$^{13}$C NMR (101 MHz, CDCl$_3$) δ173.0, 171.6, 171.2, 170.6, 160.7, 157.2, 71.7, 67.3, 67.2, 61.0, 60.1, 52.9, 43.1, 42.9, 42.8, 42.6, 25.8, 25.7, 25.4, 25.4, 22.4, 22.4
HRMS (ESI) calcd for [M+Na]$^+$ C$_{28}$H$_{44}$N$_2$O$_{10}$Na 591.2894, found 591.2847

JDW-II-008

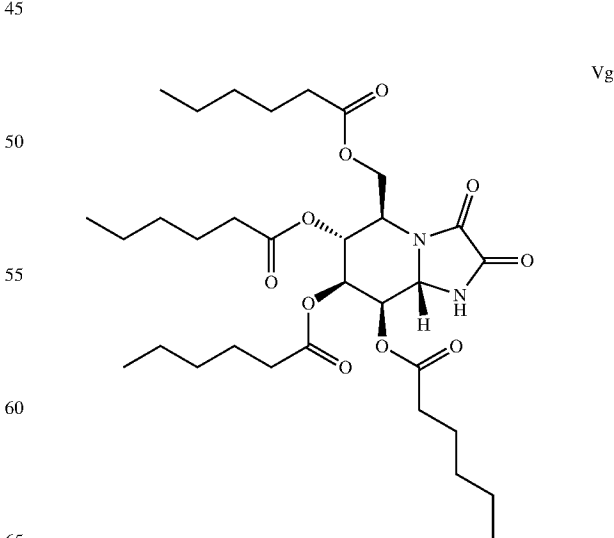

Vg

Color: White solid
Yield: 73%

$^1$H NMR (400 MHz, CDCl$_3$) δ5.49 (t, J=3.40 Hz, 1H), 5.22 (d, J=9.5 Hz, 1H), 5.08 (d, J=3.70 Hz, 1H), 4.88 (dd, J=9.40 Hz, J=3.0 Hz, 1H), 4.72 (td, J=13.70 Hz, J=12.60 Hz, J=9.80 Hz, 2H), 4.15 (dd, J=9.60 Hz, J=3.10 Hz, 1H), 2.41 (t, J=7.50 Hz, 2H), 2.36-2.22 (m, 6H), 1.71-1.53 (m, 8H), 1.42-1.16 (m, 16H), 0.99-0.79 (m, 12H)

$^{13}$C NMR (101 MHz, CDCl$_3$) δ173.7, 172.3, 172.0, 171.4, 157.3, 71.7, 67.3, 67.3, 60.9, 52.8, 34.0, 33.9, 33.9, 33.8, 31.3, 31.2, 31.2, 24.6, 24.4, 24.4, 24.3

HRMS (ESI) calcd for [M+Na]$^+$ C$_{32}$H$_{52}$N$_2$O$_{10}$Na 647.3520, found 647.3563

SK-IV-058

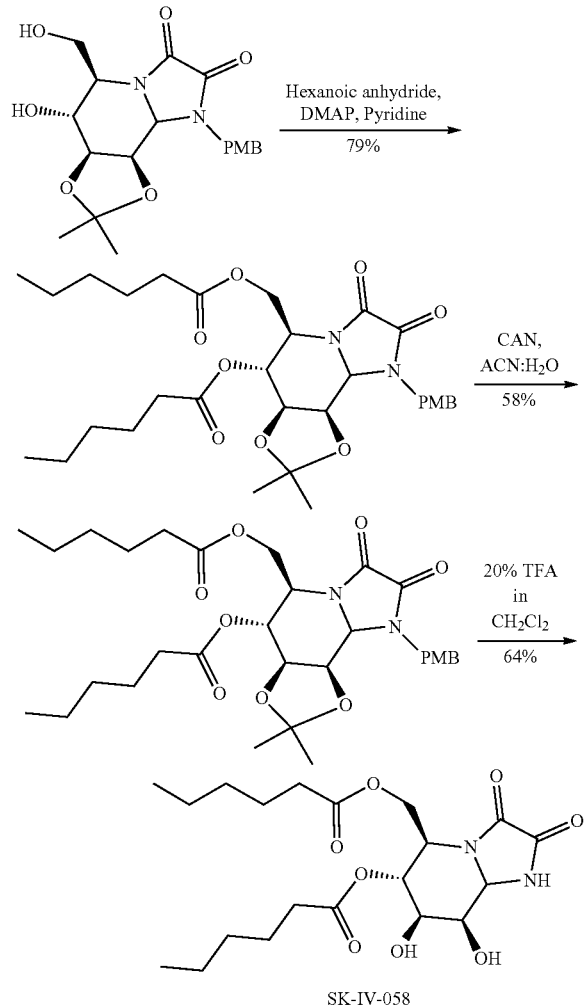

SK-IV-058

SK-IV-058 data:

$^1$H NMR (400 MHz, MeOD) δ5.17-5.06 (m, 1H), 4.57 (dd, J=10.4, 4.3 Hz, 1H), 4.25 (dd, J=11.7, 4.1 Hz, 1H), 4.04 (t, J=3.3 Hz, OH), 3.45 (dt, J=9.3, 2.9 Hz, 1H), 2.41-2.23 (m, 2H), 1.59 (tt, J=7.3, 3.3 Hz, 2H), 1.31 (dddt, J=15.5, 12.0, 8.0, 4.9 Hz, 4H), 0.91 (td, J=7.0, 4.2 Hz, 3H).

$^{13}$C NMR (101 MHz, MeOD) δ175.18, 173.75, 161.50, 160.11, 73.89, 71.81, 70.67, 64.22, 62.49, 54.20, 34.83, 34.80, 32.36, 32.29, 25.60, 25.54, 23.36, 14.27, 14.26.

HRMS (ESI) calcd for [M+Na]$^+$ C20H32N2O8Na 428.2159, Found 428.2141

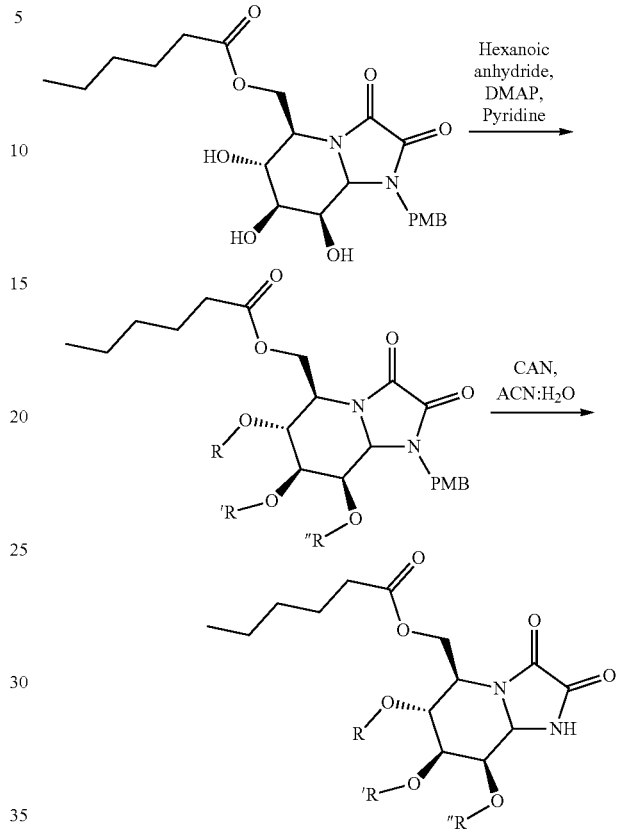

SK-IV-084A: R = OH; R' = X; R'' = OH
SK-IV-084B: R = OH; R' = OH; R'' = X
SK-IV-084C: R = X; R' = X; R'' = OH
SK-IV-084D: R = X; R' = OH; R'' = X

X =

SK-IV-084A: HRMS (ESI) calcd for [M+Na]+ C20H32N2O8Na 428.2159, Found 428.2171

SK-IV-084B: HRMS (ESI) calcd for [M+Na]+ C20H32N2O8Na 428.2159, Found 428.2164

SK-IV-084C: HRMS (ESI) calcd for [M+Na]+ C26H42N2O9Na 526.2890, Found 526.2899

SK-IV-084D: HRMS (ESI) calcd for [M+Na]+ C26H42N2O9Na 526.2890, Found 526.2903

Results

Figure 1B:
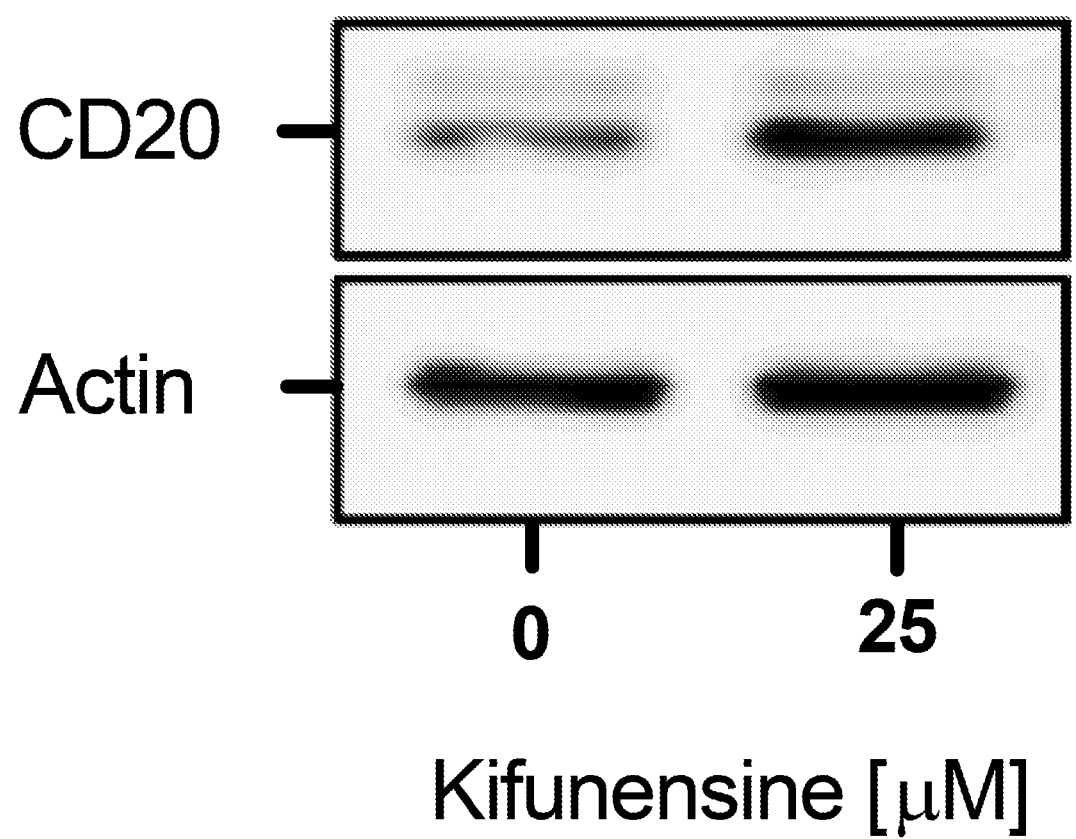
Figure 1C:
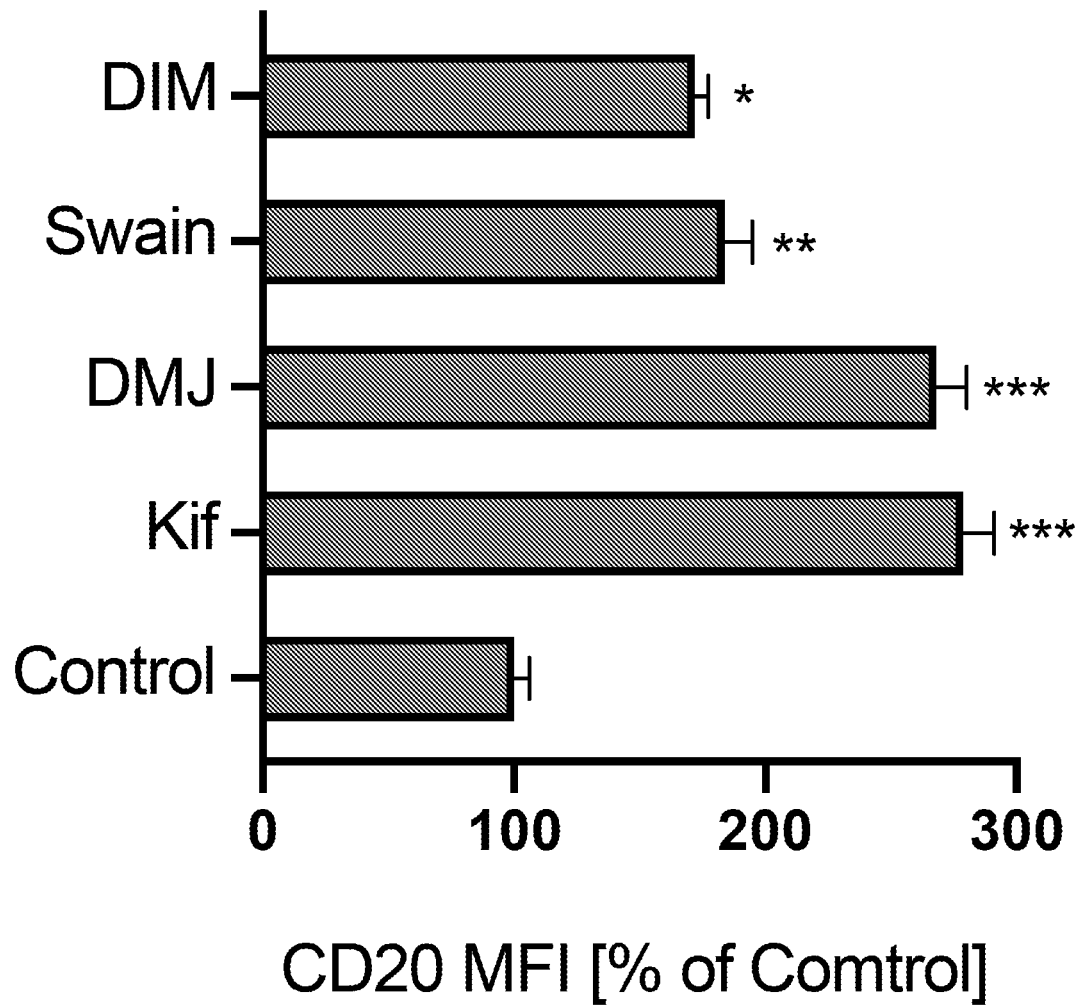
Figure 1D:
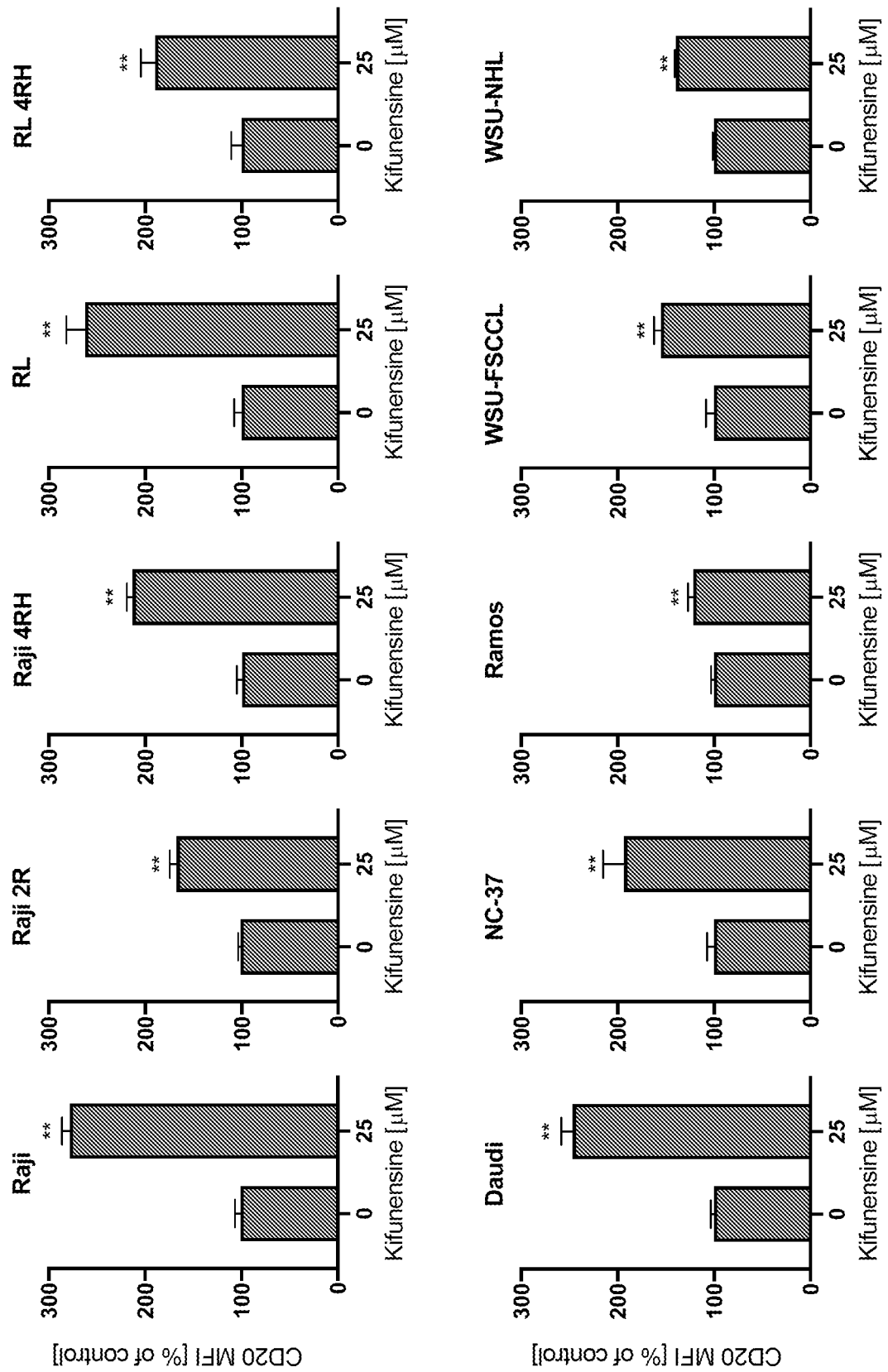
Figure 1E:
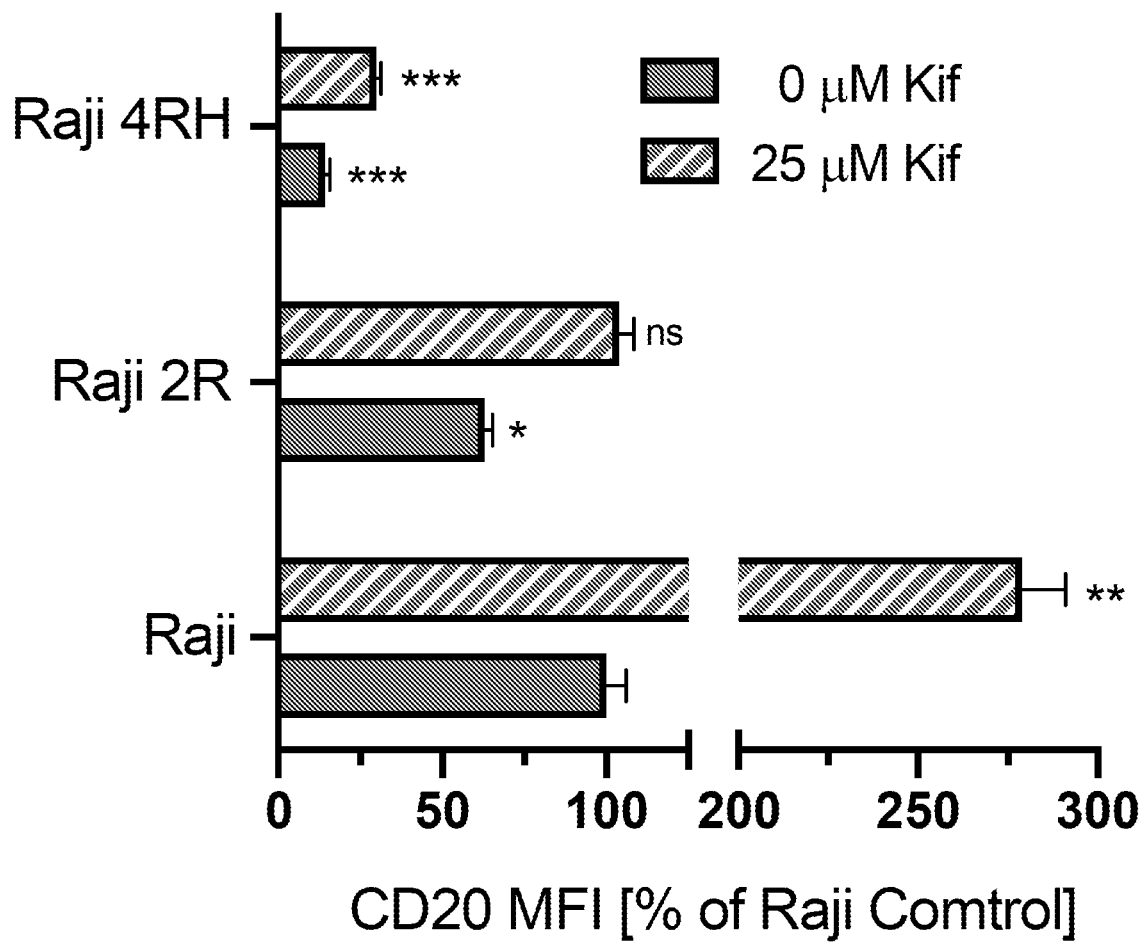

Mannosidase inhibitors upregulate CD20 expression. The type I α-mannosidase inhibitor kifunensine ("Kif:") increases cell surface expression of CD20 in Raji cells in a concentration dependent manner was determined by flow cytometry (FIG. 1A). The ability of Kif to increase CD20 expression was confirmed by western blotting (FIG. 1B). Furthermore, the structurally distinct α-mannosidase inhibitors deoxymannojirimycin (DMJ), swainsonine (Swain), and 1,4-dideoxy-1,4-imino-D-mannitol (DIM) also significantly increase CD20 expression, but interestingly, it is evident that the type I α-mannosidase inhibitors Kif and DMJ upregulate CD20 to a greater extent than type II α-mannosidase inhibitors Swain and DIM (FIG. 1C). Further studies demonstrate that Kif upregulates CD20 in a panel of cells lines representing diffuse large B cell lymphoma, Burkitt lymphoma, and follicular lymphoma (FIG. 1D). In all cases the upregulation of CD20 by Kif is statistically significant relative to the control, however, effects were less pronounced in Ramos, WSU-FSCCL and WSU-NHL cell lines. Importantly, Kif significantly increased CD20 expression in rituximab resistant cell lines (i.e., Raji 2R, Raji 4RH, and RL 4RH), and in the case of Raji 2R cells CD20 expression after treatment with Kif was statistically indistinguishable from the parental Raji cell (FIG. 1E). Furthermore, using patient derived primary CLL samples it was observed that Kif increases CD20 expression in a dose-dependent and significant manner. Taken together these data demonstrate that mannosidase inhibitors upregulate CD20 in established cell lines, rituximab resistant cell lines, primary samples.

Figure 2A:
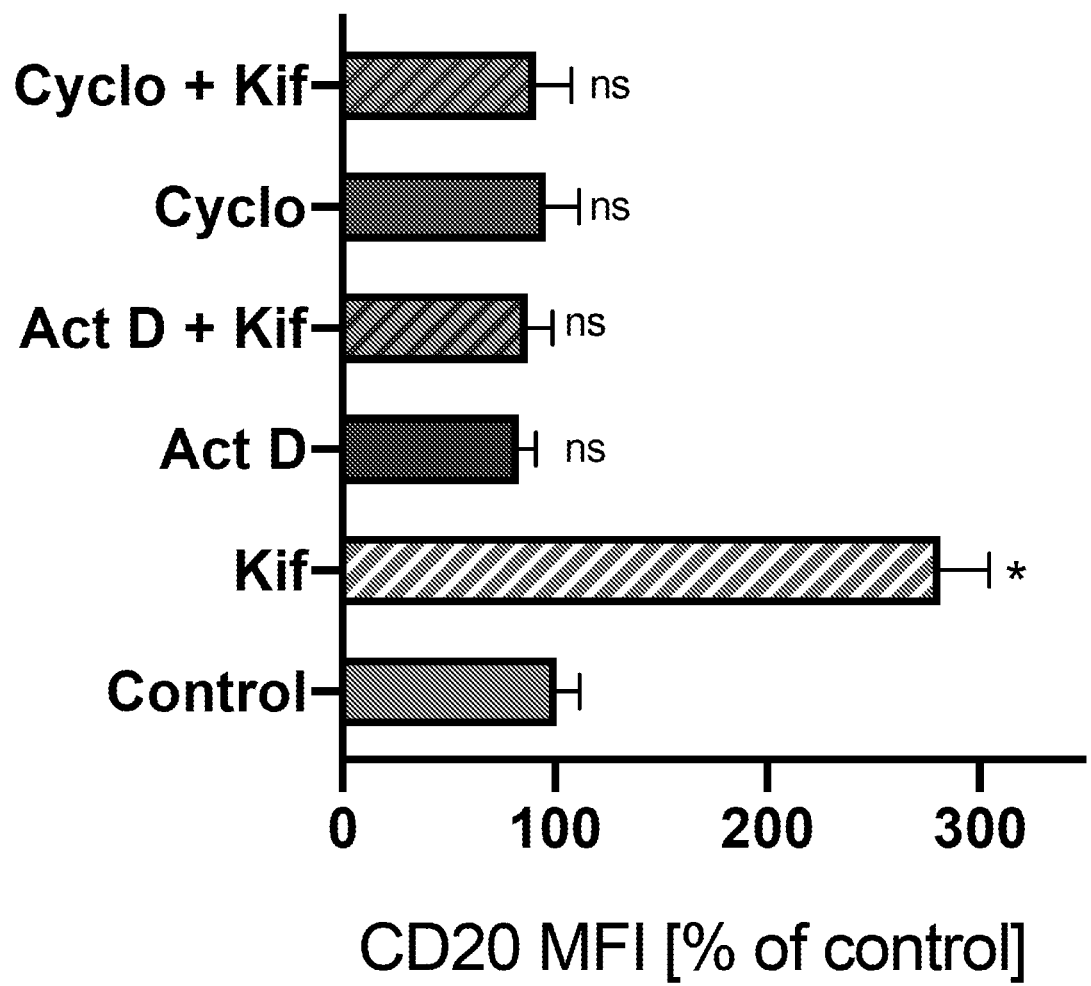
FIGS. 2A-2B illustrates that Kif mediates CD20 upregulation occurs upstream of transcription and translation. Cells were incubated with Kif (25 µM), Kif (25 µM) plus actinomycin D (10 µg/ml), Kif (25 µM) plus cycloheximide (100 µg/ml), or vehicle control (Con) for 48 hours and the cell surface levels of CD20 were analyzed by flow cytometry (FIG. 2A). Cells were incubated with Kif (25 µM) or vehicle control (Con) for 48 hours and CD20 mRNA levels were analyzed by RT-PCR (FIG. 2B).
Figure 2B:
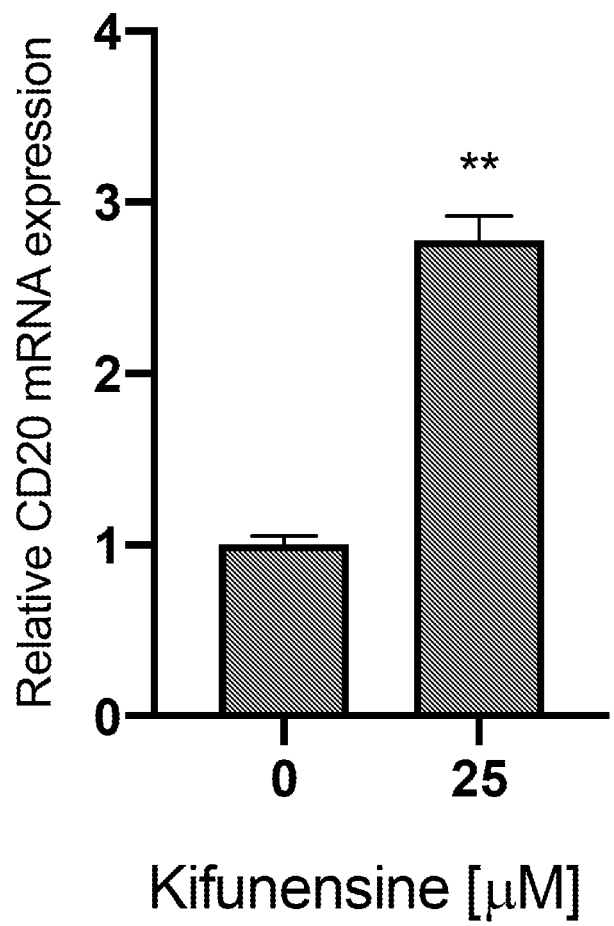

Kifunensine alters CD20 expression at a transcriptional level (FIGS. 2A-2B). CD20 is a non-glycosylated protein, as such, the mechanism by which Kif induces CD20 expression is not evident. First, we investigated if inhibiting transcription and translation, using actinomycin D (ACT-D) and cycloheximide (CHX) respectively, hindered Kif induced upregulation of CD20. Interestingly, both molecules were shown to inhibit Kif mediated CD20 upregulation, thus suggesting that Kif is impacting MS4A1 transcription (i.e., the CD20 encoding gene). This was confirmed by with the observation that treating Raji cells with Kif altered the expression of the MS4A1. A number of compounds that have been previously reported to increase MS4A1 expression have been shown to alter histone acetylation, however, treating Raji cells with Kif did not significantly alter histone acetylation.

Figure 3A:
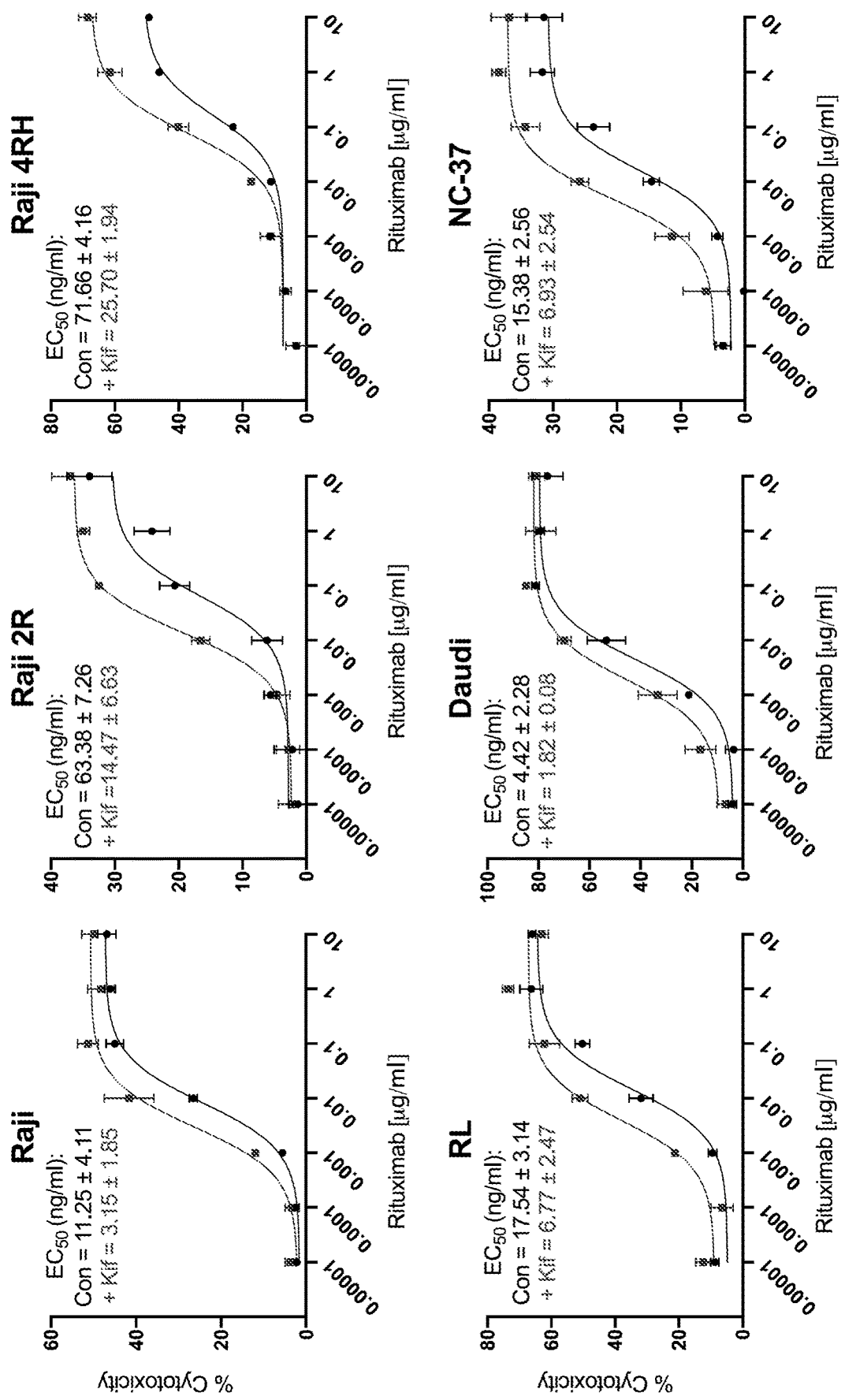
FIGS. 3A-3B illustrate Kif potentiates the activity of anti-CD20 antibodies in vitro. Cells were incubated with Kif (25 µM) or vehicle control (Con) for 48 hours prior to rituximab mediated ADCC (FIG. 3A) or CDC (FIG. 3B).
Figure 3B:
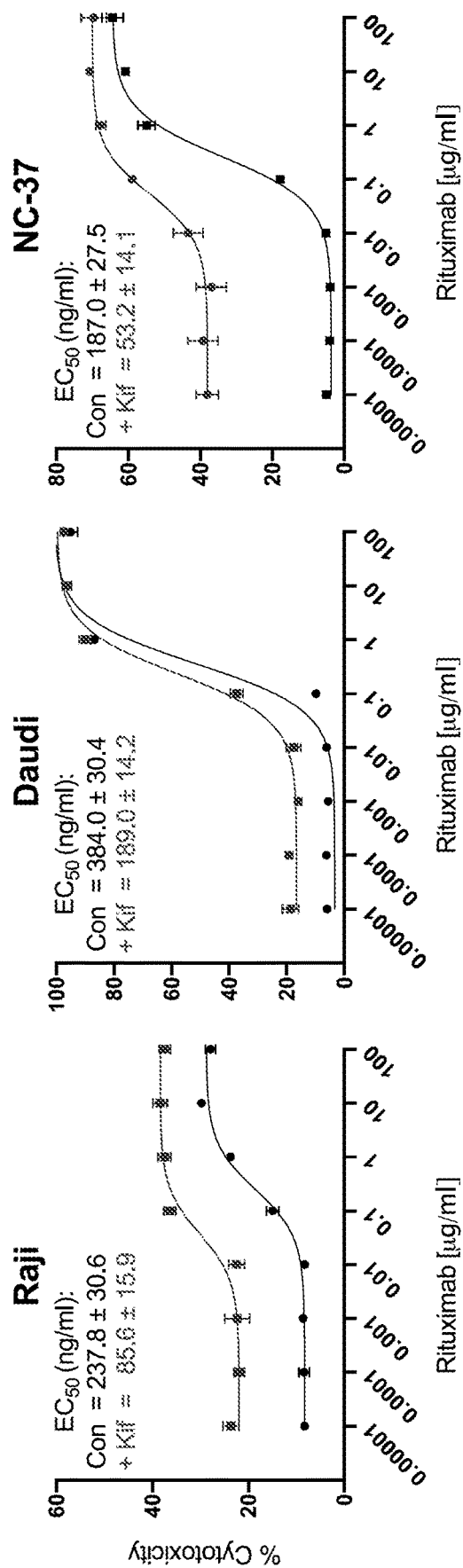

Kifunensine potentiates the activity of anti-CD20 antibodies in vitro (FIGS. 3A-3B). We next investigated if increasing CD20 expression with Kif sensitizes cell lines to anti-CD20 antibodies. In all cell lines tested we observed that the potency of rituximab was increased when applied in combination with Kif in antibody dependent cellular cytotoxicity (ADCC) assays. Importantly, the Raji-derived rituximab resistant cell lines, Raji 2R and Raji 4RH, are both sensitized to the action of rituximab when treated with Kif, and the observed resulted are in line with the CD20 expression data outlined above, as treating Raji 2R cells with Kif renders these cells equally sensitive to the parental Raji cell line. Furthermore, the potency of obinutuzumab was also increased when this antibody was applied in combination with Kif. Additionally, treating cells with Kif prior to complement dependent cytotoxicity (CDC) assays rendered cells more susceptible to with both rituximab and ofatumumab. Interestingly, Kif treated cells were more susceptible to complement mediated killing in the absence of antibody, which suggests activation of the lectin complement pathway due the increased prevalence of high mannose glycans on cell surfaces upon treatment with Kif. Unfortunately, rituximab resistant cells were not sensitized to CDC upon treatment with Kif (data not shown). This likely occurs as these resistant cell lines are prepared by culturing the parental cell lines to low levels of rituximab and human complete for extended periods of time, leading to the down regulation of CD20 and the upregulation of complement inhibitory proteins.[20]

In vivo increase in CD20 expression of Raji cells and Rituximab resistant Raji 4RH cells. A study was performed to determine whether Kif can increase the expression of CD20 on Raji cells and Rituximab resistant Raji 4RH cells that had been subcutaneously inoculated into the flank of six week old SCID mice. After inoculation, tumors were permitted to grow for 10 days prior to treatment initiation. The mice were randomly divided into control and treatment groups. Control group received PBS, while the treatment group received Kif (i.p., 10 mg/kg) every second day over an 8 day period. The mice were then scarified, tumors were harvested, and CD20 expression was assessed by Western blot. It was evident from both blots that treatment with Kif increases the expression of CD20, including the increase in CD20 in the rituximab resistant Raji 4RH cell line. It is also important to note that no side effects were observed upon treating mice with Kif.

Compounds of the Present Technology versus Kifunensine. Raji cells or Jurkat cells were treated with different concentrations of Kif, different concentrations of an exemplary compound of the present technology, or with vehicle in complete media for 48 hours. The cells were then washed with CarboFree blocking buffer (Vector Laboratories) and then stained with 0.25 µg/ml Cyt-CVNH MB 488 for 1 hour at 4° C. Subsequently, the treated cells were washed twice with flow buffer (PBS containing 0.5% BSA and 0.1% sodium azide) and analyzed by flow cytometry. The fold change in staining was assessed relative to DMSO treated controls and $EC_{50}$ values were generated by plotting fold change versus concentration. Results are provided below:

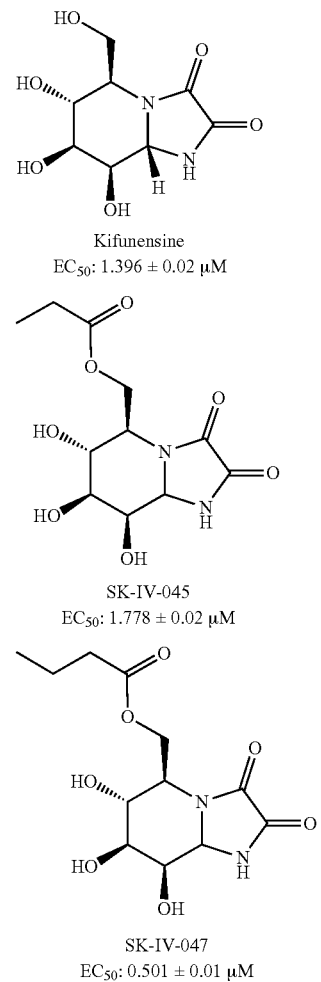

Kifunensine
$EC_{50}$: 1.396 ± 0.02 µM

SK-IV-045
$EC_{50}$: 1.778 ± 0.02 µM

SK-IV-047
$EC_{50}$: 0.501 ± 0.01 µM

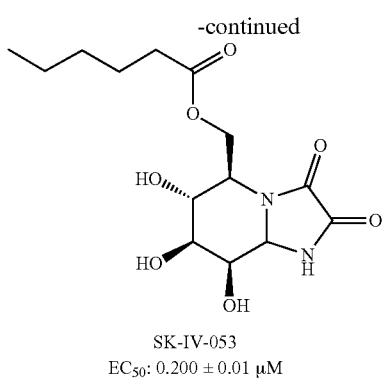

SK-IV-053
EC$_{50}$: 0.200 ± 0.01 μM

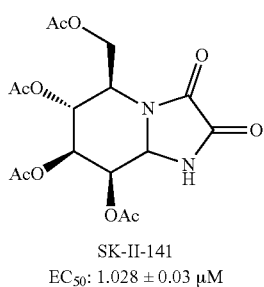

SK-II-141
EC$_{50}$: 1.028 ± 0.03 μM

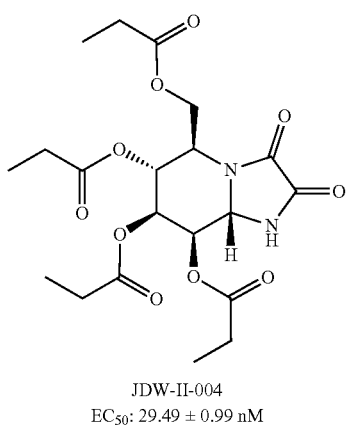

JDW-II-004
EC$_{50}$: 29.49 ± 0.99 nM

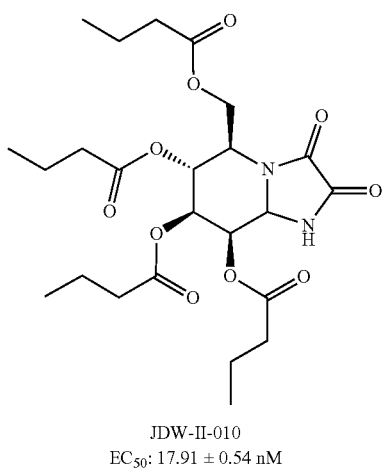

JDW-II-010
EC$_{50}$: 17.91 ± 0.54 nM

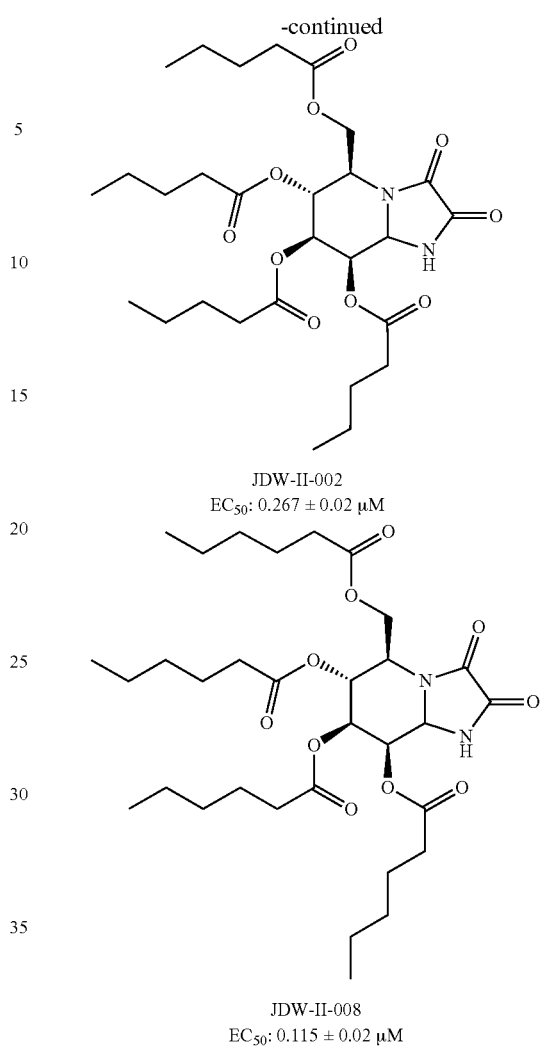

JDW-II-002
EC$_{50}$: 0.267 ± 0.02 μM

JDW-II-008
EC$_{50}$: 0.115 ± 0.02 μM

|            | Raji EC$_{50}$ nM | Jurkat EC$_{50}$ nM |
|------------|-------------------|---------------------|
| SK-IV-086  | 23.45             | 12.09               |
| SK-IV-084A | 34.23             | NT                  |
| SK-IV-084B | 41.11             | NT                  |
| SK-IV-084C | 82.25             | NT                  |
| SK-IV-084D | 98.53             | NT                  |

NT = not yet tested

Application of Compounds of the Present Technology

Intratumoral injection of compounds of the present technology solubilized in an oil (e.g., sesame oil) is expected to lead to the formation of a depot of compound in the tumor. Leaching of the compound from the depot will permit local uptake by the cancer cells in the tumor, which in turn will lead to the desertification of the compounds of the present technology by esterase's to provide Kif. Kif will then be capable of disrupting the N-glycosylation pathways which leads to the increased prevalence of high mannose N-glycans on the surface of these malignant cells. These high mannose N-glycans may then be recognized by receptors on immune cells and are expected to lead to immune cell stimulation in the tumor. Silva M C, Fernandes Â, Oliveira M, Resende C, Correia A, de-Freitas-Junior J C, Lavelle A, Andrade-da-Costa J, Leander M, Xavier-Ferreira H, Bessa J, Pereira C, Henrique R M, Carneiro F, Dinis-Ribeiro M, Marcos-Pinto R, Lima M, Lepenies B, Sokol H, Machado J C, Vilanova M, Pinho S S. "Glycans as Immune Checkpoints: Removal of Branched N-glycans Enhances Immune Recognition Preventing Cancer Progression". *Cancer Immunol Res.* 2020; 8(11):1407-25. doi: 10.1158/2326-6066.Cir-20-0264. PubMed PMID: 32933968. Alternatively or in addition to the above, proteins that bind specifically to high mannose N-glycan can be utilized to deliver cytotoxic payloads to high mannose N-glycans coated cancer cells. As such, the compounds of the present technology may render the malignant cells sensitive to the protein toxin conjugates.

Prophetic Animal Study Including a High Mannose N-Glycan Specific Lectin

Balb/c mice will be subcutaneously inoculated with CT26 cells on one flank and the tumors will be permitted to grown for a period of 6 days. At this point, a compound of the present technology, solubilized in an oil, will be delivered intratumorally (0.2-1 mg of compound/dose), and dosing will continue every 3 days. On day 9, animals will be dosed with a compound of the present technology, in addition to a high mannose N-glycan specific lectin (cyanovirin-N) that has been modified to carry a cytotoxic payload (e.g., MMAE or MMAF). Animal will continue to be dosed every 3 days with both the compound of the present technology and the lectin drug conjugate until a maximum volume of 1800 cm$^3$. At this point, mice will be euthanized in accordance to an established protocol that has been approved the ACU.

Prophetic Animal Studies Utilizing Various Lymphoma Cell Lines

These studies will probe whether kifunensine and compounds of the present technology can enhance rituximab activity using several lymphoma animal models. These studies will utilize the following readily available lymphoma mouse models: 1) lymphoma xerographs mouse models using rituximab sensitive and resistant cell lines (using cell lines representative of different lymphoma subtypes [diffuse large B cell lymphoma, Burkitt's lymphoma, or mantle cell lymphoma] and 2) patient-derived xenograft (PDX) mouse models using primary tumor samples isolated from previously untreated, rituximab sensitive or resistant B cell lymphoma patients. All in vivo experiments will use six weeks old SCID-female mice. To evaluate changes in CD20 expression following kifunensine treatment or treatment with a compound of the present technology, SCID mice will be inoculated via tail vein injection with 1×10$^6$ NHL cell lines (Raji, Raji 4RH, etc.) or implanted with primary tumors harvested from B cell lymphoma patients. Upon tumor engraftment (3 days for animals injected with cell lines via tail vein injection or once a palpable tumor is observed in PDX models), animals will be then treated with PBS (control), kifunensine, or a compound of the present technology. After 48 hrs. of drug exposure, animals will be sacrificed and organs (e.g., liver, lung, and spleen in cell line inoculated animals) or primary tumor (PDX models) will be collected. Changes in human CD20 expression will be evaluated by immunohistochemistry, flow cytometry, and Western Blotting.

For experiments using cell lines, mice will be inoculated with 1×10$^6$ NHL -Luc/GFP cells (i.e., Raji, Raji 4RH, etc.) per mouse by tail vein injection. Mice will then be randomized to receive via tail vein injection either PBS (control), kifunensine alone, a compound of the present technology alone, rituximab alone, isotype control, kifunensine+rituximab combination, a compound of the present technology+rituximab combination, kifunensine and isotype control, or a compound of the present technology and isotype control. Therapy will be given 3 days after tumor inoculation to ensure tumors are fully engrafted. Mice will be imaged on an IVIS Spectrum animal imager starting on day 7 and continuing weekly until death or experiment termination. The primary end point of the study will be survival, defined as the time to development of limb paralysis. SCID mice that respond to treatment will be sacrificed after a 150-day period of observation. Tumors are expected to grow systemically, predominantly in the lung parenchyma. Death, moribund condition, morbidity, and tumor burden are not endpoints in these experiments. The experiments will last approximately 150 days, at the end of which the mice will be sacrificed by cervical dislocation. If, however, an animal appears to exhibit signs of the above conditions due to treatment, or other reasons it will be sacrificed immediately to prevent any further suffering. Early signs of illness including ruffled fur gait imbalance and slight weight loss will be good indicators to warrant intervention. Euthanasia by cervical dislocation will be used, since $CO_2$ and/or anesthesia may interfere with the experiment results.

For PDX mouse model's primary tumor will be harvested from previously untreated, rituximab sensitive and rituximab resistant lymphoma patients. Tumors will be implanted and propagated in 6-8 SCID mice. Once tumors reach 0.5 mm in diameter cohorts of animals will be treated with PBS, kifunensine, a compound of the present technology, rituximab, isotype control, kifunensine+rituximab, kifunensine+isotype control, a compound of the present technology+rituximab, or a compound of the present technology+isotype control. Serial tumor measurements will be recorded every 48 hrs. Once the tumors reach the size of 2 cm×2 cm, animals will be euthanized as described above. Differences in rate of tumor growth will be compared across treatment arms.

REFERENCES

1. Bray F, Ferlay J, Soerjomataram I, Siegel R L, Torre L A, Jemal A. Global cancer statistics 2018: GLOBOCAN estimates of incidence and mortality worldwide for 36 cancers in 185 countries. CA Cancer J Clin. 2018; 68(6): 394-424. PubMed PMID: 30207593.
2. Tun A M, Ansell S M. Immunotherapy in Hodgkin and non-Hodgkin lymphoma: Innate, adaptive and targeted immunological strategies. Cancer Treat Rev. 2020; 88:102042. PubMed PMID: 32521386.
3. Neumann F, Harmsen S, Martin S, Kronenwett R, Kondakci M, Aivado M, Germing U, Haas R, Kobbe G. Rituximab long-term maintenance therapy after autologous stem cell transplantation in patients with B-cell non-Hodgkin's lymphoma. Ann Hematol. 2006; 85(8): 530-4. PubMed PMID: 16639571.
4. Khouri I F, McLaughlin P, Saliba R M, Hosing C, Korbling M, Lee M S, Medeiros L J, Fayad L, Samaniego F, Alousi A, Anderlini P, Couriel D, de Lima M, Giralt S, Neelapu S S, Ueno N T, Samuels B I, Hagemeister F, Kwak L W, Champlin R E. Eight-year experience with allogeneic stem cell transplantation for relapsed follicular lymphoma after nonmyeloablative conditioning with fludarabine, cyclophosphamide, and rituximab. Blood. 2008; 111(12):5530-6. PubMed PMID: 18411419; PMCID: PMC4624452.
5. Khouri I F, Saliba R M, Hosing C, Okoroji G J, Acholonu S, Anderlini P, Couriel D, De Lima M, Donato M L, Fayad L, Giralt S, Jones R, Korbling M, Maadani F, Manning J T, Pro B, Shpall E, Younes A, McLaughlin P, Champlin R E. Concurrent administration of high-dose rituximab before and after autologous stem-cell transplantation for relapsed aggressive B-cell non-Hodgkin's lymphomas. J Clin Oncol. 2005; 23(10):2240-7. PubMed PMID: 15800314.
6. McLaughlin P, Grillo-López A J, Link B K, Levy R, Czuczman M S, Williams M E, Heyman M R, Bence-Bruckler I, White C A, Cabanillas F, Jain V, Ho A D, Lister J, Wey K, Shen D, Dallaire B K. Rituximab chimeric anti-CD20 monoclonal antibody therapy for relapsed indolent lymphoma: half of patients respond to a four-dose treatment program. J Clin Oncol. 1998; 16(8): 2825-33. PubMed PMID: 9704735.
7. Smith M R. Rituximab (monoclonal anti-CD20 antibody): mechanisms of action and resistance. Oncogene. 2003; 22(47):7359-68. PubMed PMID: 14576843.
8. Golay J, Lazzari M, Facchinetti V, Bernasconi S, Borleri G, Barbui T, Rambaldi A, Introna M. CD20 levels determine the in vitro susceptibility to rituximab and complement of B-cell chronic lymphocytic leukemia: further regulation by CD55 and CD59. Blood. 2001; 98(12): 3383-9. PubMed PMID: 11719378.
9. van Meerten T, van Rijn R S, Hol S, Hagenbeek A, Ebeling S B. Complement-induced cell death by rituximab depends on CD20 expression level and acts complementary to antibody-dependent cellular cytotoxicity. Clin Cancer Res. 2006; 12(13):4027-35. PubMed PMID: 16818702.
10. Sarro S M, Unruh T L, Zuccolo J, Sanyal R, Luider J M, Auer-Grzesiak I A, Mansoor A, Deans J P. Quantification of CD20 mRNA and protein levels in chronic lymphocytic leukemia suggests a post-transcriptional defect. Leuk Res. 2010; 34(12):1670-3. PubMed PMID: 20674973.
11. Ginaldi L, De Martinis M, Matutes E, Farahat N, Morilla R, Catovsky D. Levels of expression of CD19 and CD20 in chronic B cell leukaemias. J Clin Pathol. 1998; 51(5): 364-9. PubMed PMID: 9708202; PMCID: PMC500695.
12. Mankaï A, Bordron A, Renaudineau Y, Martins-Carvalho C, Takahashi S, Ghedira I, Berthou C, Youinou P. Purine-rich box-1-mediated reduced expression of CD20 alters rituximab-induced lysis of chronic lymphocytic leukemia B cells. Cancer Res. 2008; 68(18):7512-9. PubMed PMID: 18794139.
13. Kinoshita T, Nagai H, Murate T, Saito H. CD20-negative relapse in B-cell lymphoma after treatment with Rituximab. J Clin Oncol. 1998; 16(12):3916. PubMed PMID: 9850038.
14. Kennedy G A, Tey S K, Cobcroft R, Marlton P, Cull G, Grimmett K, Thomson D, Gill D. Incidence and nature of CD20-negative relapses following rituximab therapy in aggressive B-cell non-Hodgkin's lymphoma: a retrospective review. Br J Haematol. 2002; 119(2):412-6. PubMed PMID: 12406079.
15. Bonavida B. Postulated mechanisms of resistance of B-cell non-Hodgkin lymphoma to rituximab treatment regimens: strategies to overcome resistance. Semin Oncol. 2014; 41(5):667-77. PubMed PMID: 25440611; PMCID: PMC4254685.
16. Davis T A, Czerwinski D K, Levy R. Therapy of B-cell lymphoma with anti-CD20 antibodies can result in the loss of CD20 antigen expression. Clin Cancer Res. 1999; 5(3):611-5. PubMed PMID: 10100713.
17. Pickartz T, Ringel F, Wedde M, Renz H, Klein A, von Neuhoff N, Dreger P, Kreuzer K A, Schmidt C A, Srock S, Schoeler D, Schriever F. Selection of B-cell chronic lymphocytic leukemia cell variants by therapy with anti-CD20 monoclonal antibody rituximab. Exp Hematol. 2001; 29(12):1410-6. PubMed PMID: 11750099.
18. Hiraga J, Tomita A, Sugimoto T, Shimada K, Ito M, Nakamura S, Kiyoi H, Kinoshita T, Naoe T. Down-regulation of CD20 expression in B-cell lymphoma cells after treatment with rituximab-containing combination chemotherapies: its prevalence and clinical significance. Blood. 2009; 113(20):4885-93. PubMed PMID: 19246561.
19. Jilani I, O'Brien S, Manshuri T, Thomas D A, Thomazy V A, Imam M, Naeem S, Verstovsek S, Kantarjian H, Giles F, Keating M, Albitar M. Transient down-modulation of CD20 by rituximab in patients with chronic lymphocytic leukemia. Blood. 2003; 102(10):3514-20. PubMed PMID: 12893761.
20. Czuczman M S, Olejniczak S, Gowda A, Kotowski A, Binder A, Kaur H, Knight J, Starostik P, Deans J, Hernandez-Ilizaliturri F J. Acquirement of rituximab resistance in lymphoma cell lines is associated with both global CD20 gene and protein down-regulation regulated at the pretranscriptional and posttranscriptional levels. Clin Cancer Res. 2008; 14(5):1561-70. PubMed PMID: 18316581.
21. Olejniczak S H, Hernandez-Ilizaliturri F J, Clements J L, Czuczman M S. Acquired resistance to rituximab is associated with chemotherapy resistance resulting from decreased Bax and Bak expression. Clin Cancer Res. 2008; 14(5):1550-60. PubMed PMID: 18316580.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound according to Formula I

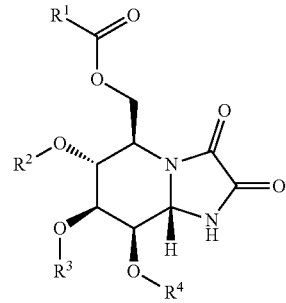

(I)

or a pharmaceutically acceptable salt and/or solvate thereof, wherein
R$^1$ is an unsubstituted C$_1$-C$_{12}$ alkyl; and
R$^2$, R$^3$, and R$^4$ are each independently H or —C(O)-(unsubstituted C$_1$-C$_{12}$ alkyl).

B. The compound of Paragraph A, wherein R$^1$ is an unsubstituted C$_1$-C$_6$ alkyl.

C. The compound of Paragraph A or Paragraph B, wherein R$^2$, R$^3$, and R$^4$ are each independently H or —C(O)-(unsubstituted C$_1$-C$_6$ alkyl).

D. The compound of any one of Paragraphs A-C, wherein R$^1$ is CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH$_2$CH$_2$CH$_2$CH$_2$CH$_3$, or CH$_2$CH$_2$CH(CH$_3$)$_2$.

E. The compound of any one of Paragraphs A-D, wherein R$^2$, R$^3$, and R$^4$ are each independently H, —C(O)CH$_3$, —C(O)CH$_2$CH$_3$, —C(O)CH$_2$CH$_2$CH$_3$, —C(O)CH(CH$_3$)$_2$, —C(O)CH$_2$CH$_2$CH$_2$CH$_3$, —C(O)CH$_2$CH(CH$_3$)$_2$, —C(O)CH$_2$CH$_2$CH$_2$CH$_2$CH$_3$, or —C(O)CH$_2$CH$_2$CH(CH$_3$)$_2$.

F. The compound of any one of Paragraphs A-E, wherein the compound is of Formula Ia

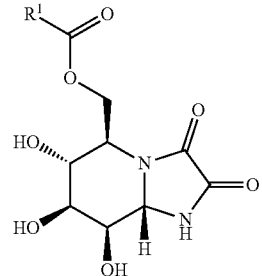

(Ia)

or a pharmaceutically acceptable salt and/or solvate thereof; of Formula Ib

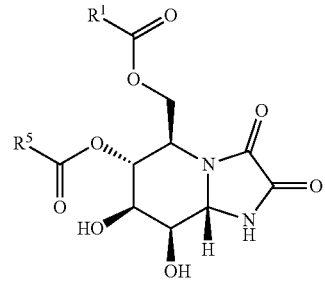

(Ib)

or a pharmaceutically acceptable salt and/or solvate thereof; of Formula Ic

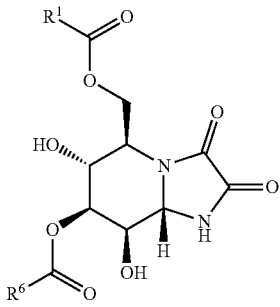

(Ic)

or a pharmaceutically acceptable salt and/or solvate thereof; of Formula Id

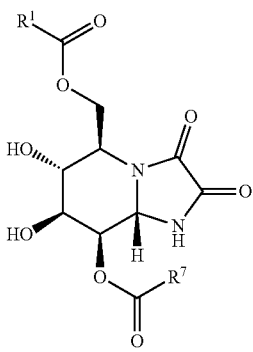

(Id)

or a pharmaceutically acceptable salt and/or solvate thereof; of Formula Ie

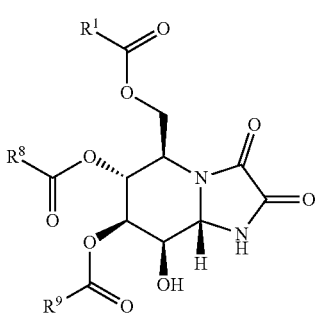

(Ie)

or a pharmaceutically acceptable salt and/or solvate thereof; of Formula If

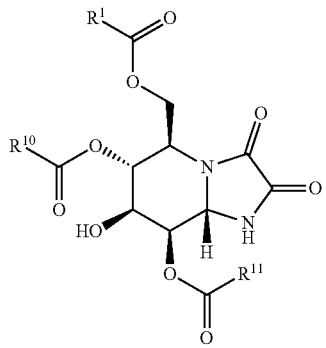

(If)

or a pharmaceutically acceptable salt and/or solvate thereof; or of Formula Ig (Ig)

or a pharmaceutically acceptable salt and/or solvate thereof;
wherein $R^5$, $R^6$, $R^7$, $R^8$, $R^9$, $R^{10}$, $R^{11}$, $R^{12}$, $R^{13}$, and $R^{14}$ are each independently an unsubstituted $C_1$-$C_{12}$ alkyl.

G. The compound of any one of Paragraphs A-F, wherein $R^5$, $R^6$, $R^7$, $R^8$, $R^9$, $R^{10}$, $R^{11}$, $R^{12}$, $R^{13}$, and $R^{14}$ are each independently an unsubstituted $C_1$-$C_6$ alkyl.

H. The compound of any one of Paragraphs A-G, wherein $R^5$, $R^6$, $R^7$, $R^8$, $R^9$, $R^{10}$, $R^{11}$, $R^{12}$, $R^{13}$, and $R^{14}$ are each independently $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

I. The compound of any one of Paragraphs F-H, wherein the compound is of Formula Ib and each of $R^1$ and $R^5$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

J. The compound of any one of Paragraphs F-H, wherein the compound is of Formula Ic and each of $R^1$ and $R^6$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

K. The compound of any one of Paragraphs F-H, wherein the compound is of Formula Id and each of $R^1$ and $R^7$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

L. The compound of any one of Paragraphs F-H, wherein the compound is of Formula Ie and each of $R^1$, $R^8$, and $R^9$ is CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH$_2$CH$_2$CH$_2$CH$_2$CH$_3$, or CH$_2$CH$_2$CH(CH$_3$)$_2$.

M. The compound of any one of Paragraphs F-H, wherein the compound is of Formula If and each of R$^1$, R$^{10}$, and R$^{11}$ is CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH$_2$CH$_2$CH$_2$CH$_2$CH$_3$, or CH$_2$CH$_2$CH(CH$_3$)$_2$.

N. The compound of any one of Paragraphs F-H, wherein the compound is of Formula Ig and each of R$^1$, R$^{12}$, R$^{13}$, and R$^{14}$ is CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH$_2$CH$_2$CH$_2$CH$_2$CH$_3$, or CH$_2$CH$_2$CH(CH$_3$)$_2$.

O. A composition comprising a compound of any one of Paragraphs A-N and a pharmaceutically acceptable carrier.

P. A pharmaceutical composition comprising a pharmaceutically acceptable carrier and an effective amount of a compound of any one of Paragraphs A-N, wherein the effective amount of the compound is effective to treat a B-cell malignancy.

Q. A pharmaceutical composition comprising a pharmaceutically acceptable carrier and a compound of any one of Paragraphs A-N, wherein the compound is present in an amount effective to treat a B-cell malignancy when combined with an anti-CD20 monoclonal antibody.

R. The pharmaceutical composition of Paragraph Q, wherein the anti-CD20 monoclonal antibody comprises one or more of rituximab, Y90-ibritumomab, tositumomab, reditux, veltuzumab, ocaratuzumab, PRO131921,ublituzimab, TRU-015, ofatumumab, obinutuzumab, and ocrelizumab.

S. The pharmaceutical composition of Paragraph Q or Paragraph R, wherein the anti-CD20 monoclonal antibody comprises one or more of rituximab, ofatumumab, obinutuzumab, and ocrelizumab.

T. A method of treating a subject suffering from a B-cell malignancy, the method comprising administering to the subject an effective amount of a compound of any one of Paragraphs A-N and an effective amount of an anti-CD20 monoclonal antibody.

U. The method of Paragraph T, wherein the anti-CD20 monoclonal antibody comprises one or more of rituximab, Y90-ibritumomab, tositumomab, reditux, veltuzumab, ocaratuzumab, PRO131921,ublituzimab, TRU-015, ofatumumab, obinutuzumab, and ocrelizumab.

V. The method of Paragraph T or Paragraph U, wherein the anti-CD20 monoclonal antibody comprises one or more of rituximab, ofatumumab, obinutuzumab, and ocrelizumab.

W. The method of any one of Paragraphs T-V, wherein the B-cell malignancy is non-Hodgkin lymphoma or chronic lymphocytic leukemia.

X. A medicament for treating a B-cell malignancy in a subject, the medicament comprising a compound of any one of Paragraphs A-N.

Y. The medicament of Paragraph X, wherein the medicament further comprises a pharmaceutically acceptable carrier.

Z. The medicament of Paragraph X or Paragraph Y, wherein the medicament comprises an effective amount of the compound for treating the B-cell malignancy when combined with an anti-CD20 monoclonal antibody.

AA. The medicament of any one of Paragraphs X-Z, wherein the anti-CD20 monoclonal antibody comprises one or more of rituximab, Y90-ibritumomab, tositumomab, reditux, veltuzumab, ocaratuzumab, PRO131921,ublituzimab, TRU-015, ofatumumab, obinutuzumab, and ocrelizumab.

AB. The medicament of any one of Paragraphs X-AA, wherein the anti-CD20 monoclonal antibody comprises one or more of rituximab, ofatumumab, obinutuzumab, and ocrelizumab.

Other embodiments are set forth in the following claims, along with the full scope of equivalents to which such claims are entitled.

What is claimed is:

1. A compound according to Formula I

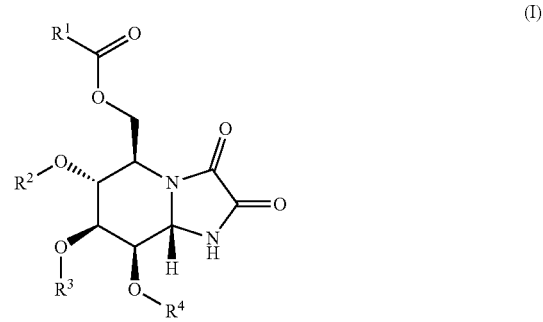

or a pharmaceutically acceptable salt thereof, wherein
R$^1$ is an unsubstituted C$_1$-C$_{12}$ alkyl; and
R$^2$, R$^3$, and R$^4$ are each independently H or —C(O)—(unsubstituted C$_1$-C$_{12}$ alkyl) wherein at least one of R$^2$, R$^3$, and R$^4$ is —C(O)—(unsubstituted C$_1$-C$_{12}$ alkyl).

2. The compound of claim 1, wherein R$^1$ is an unsubstituted C$_1$-C$_6$ alkyl.

3. The compound of claim 1, wherein R$^2$, R$^3$, and R$^4$ are each independently H or —C(O)—(unsubstituted C$_1$-C$_6$ alkyl) wherein at least one of R$^2$, R$^3$, and R$^4$ is —C(O)—(unsubstituted C$_1$-C$_6$ alkyl).

4. The compound of claim 1, wherein R$^1$ is CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH$_2$CH$_2$CH$_2$CH$_2$CH$_3$, or CH$_2$CH$_2$CH(CH$_3$)$_2$.

5. The compound of claim 1, wherein R$^2$, R$^3$, and R$^4$ are each independently H, —C(O)CH$_3$, —C(O)CH$_2$CH$_3$, —C(O)CH$_2$CH$_2$CH$_3$, —C(O)CH(CH$_3$)$_2$, —C(O)CH$_2$CH$_2$CH$_2$CH$_3$, —C(O)CH$_2$CH(CH$_3$)$_2$, —C(O)CH$_2$CH$_2$CH$_2$CH$_2$CH$_3$, or —C(O)CH$_2$CH$_2$CH(CH$_3$)$_2$, wherein at least one of R$^2$, R$^3$, and R$^4$ is —C(O)CH$_3$, —C(O)CH$_2$CH$_3$, —C(O)CH$_2$CH$_2$CH$_3$, —C(O)CH(CH$_3$)$_2$, —C(O)CH$_2$CH$_2$CH$_2$CH$_3$, —C(O)CH$_2$CH(CH$_3$)$_2$, —C(O)CH$_2$CH$_2$CH$_2$CH$_2$CH$_3$, or —C(O)CH$_2$CH$_2$CH(CH$_3$)$_2$.

6. The compound of claim 1, wherein the compound is of Formula Ib

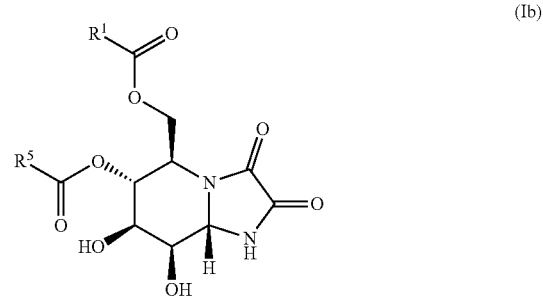

or a pharmaceutically acceptable salt thereof;
of Formula Ic

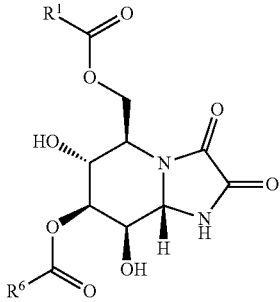

or a pharmaceutically acceptable salt thereof;
of Formula Id

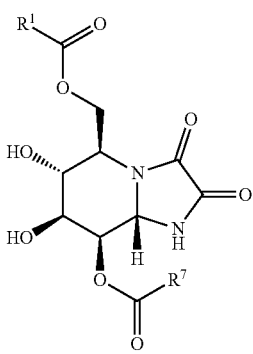

or a pharmaceutically acceptable salt thereof;
of Formula Ie

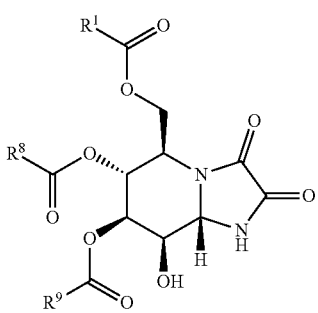

or a pharmaceutically acceptable salt thereof;
of Formula If

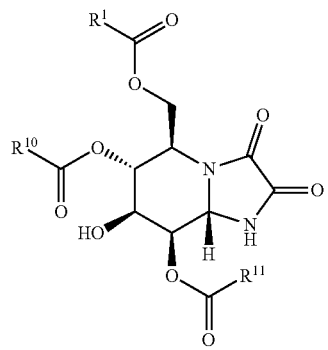

or a pharmaceutically acceptable salt thereof; or
of Formula Ig

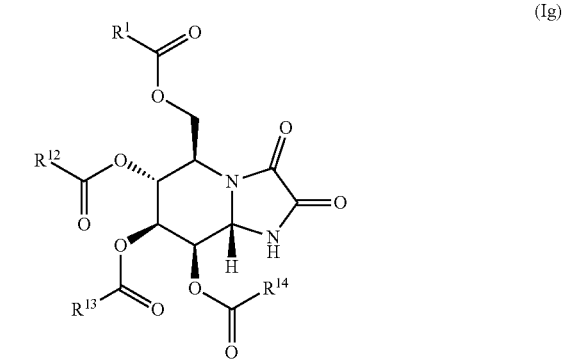

or a pharmaceutically acceptable salt thereof;
wherein $R^5$, $R^6$, $R^7$, $R^8$, $R^9$, $R^{10}$, $R^{11}$, $R^{12}$, $R^{13}$, and $R^{14}$ are each independently an unsubstituted $C_1$-$C_{12}$ alkyl.

7. The compound of claim 6, wherein $R^5$, $R^6$, $R^7$, $R^8$, $R^9$, $R^{10}$, $R^{11}$, $R^{12}$, $R^{13}$, and $R^{14}$ are each independently an unsubstituted $C_1$-$C_6$ alkyl.

8. The compound of claim 6, wherein $R^5$, $R^6$, $R^7$, $R^8$, $R^9$, $R^{10}$, $R^{11}$, $R^{12}$, $R^{13}$ and $R^{14}$ are each independently $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

9. The compound of claim 6, wherein the compound is of Formula Ib and each of $R^1$ and $R^5$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

10. The compound of claim 6, wherein the compound is of Formula Ic and each of $R^1$ and $R^6$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

11. The compound of claim 6, wherein the compound is of Formula Id and each of $R^1$ and $R^7$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

12. The compound of claim 6, wherein the compound is of Formula Ie and each of $R^1$, $R^8$, and $R^9$ is $CH_3$, $CH_2CH_3$, $CH_2CH_2CH_3$, $CH(CH_3)_2$, $CH_2CH_2CH_2CH_3$, $CH_2CH(CH_3)_2$, $CH_2CH_2CH_2CH_2CH_3$, or $CH_2CH_2CH(CH_3)_2$.

13. The compound of claim 6, wherein the compound is of Formula If and each of $R^1$, $R^{10}$, and $R^{11}$ is $CH_3$, $CH_2CH_3$, CH$_2$CH$_2$CH$_3$, CH(CH$_3$)$_2$, CH$_2$CH$_2$CH$_2$CH$_3$, CH$_2$CH(CH$_3$)$_2$, CH$_2$CH$_2$CH$_2$CH$_2$CH$_3$, or CH$_2$CH$_2$CH(CH$_3$)$_2$.

14. The compound of claim 6, wherein the compound is of Formula Ig and each of R$^1$, R$^{12}$, R$^{13}$, and R$^{14}$ is CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH$_2$CH$_2$CH$_2$CH$_2$CH$_3$, or CH$_2$CH$_2$CH(CH$_3$)$_2$.

15. A composition comprising a compound of claim 1 and a pharmaceutically acceptable carrier.

16. The compound of claim 6, wherein the compound is of Formula Ib

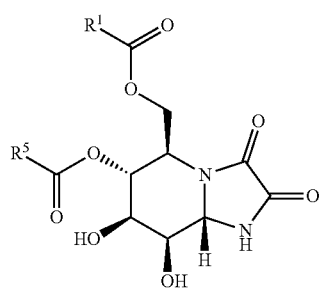

(Ib)

or a pharmaceutically acceptable salt thereof;
wherein R$^5$ is an unsubstituted C$_1$-C$_{12}$ alkyl.

17. The compound of claim 6, wherein the compound is of Formula Ic

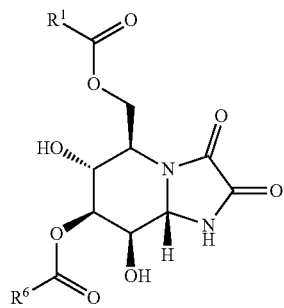

(Ic)

or a pharmaceutically acceptable salt thereof;
wherein R$^6$ is an unsubstituted C$_1$-C$_{12}$ alkyl.

18. The compound of claim 6, wherein the compound is of Formula Id

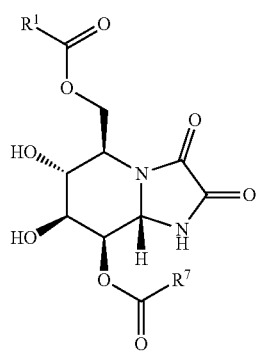

(Id)

or a pharmaceutically acceptable salt thereof;
wherein R$^7$ is an unsubstituted C$_1$-C$_{12}$ alkyl.

19. The compound of claim 6, wherein the compound is of Formula Ie

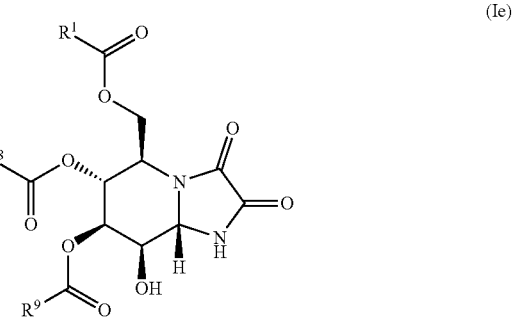

(Ie)

or a pharmaceutically acceptable salt thereof;
wherein R$^8$ and R$^9$ are each independently an unsubstituted C$_1$-C$_{12}$ alkyl.

20. The compound of claim 6, wherein the compound is of Formula If

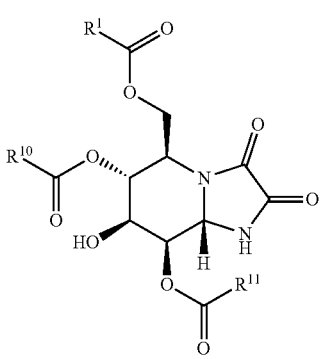

(If)

or a pharmaceutically acceptable salt thereof;
wherein R$^{10}$ and R$^{11}$ are each independently an unsubstituted C$_1$-C$_{12}$ alkyl.

21. The compound of claim 6, wherein the compound is of Formula Ig

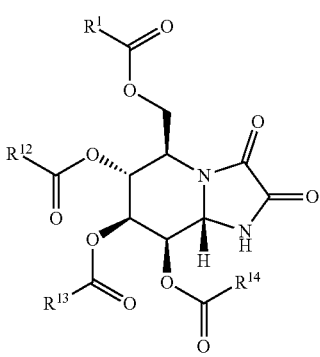

(Ig)

or a pharmaceutically acceptable salt thereof;
wherein $R^{12}$, $R^{13}$, and $R^{14}$ each independently an unsubstituted $C_1$-$C_{12}$ alkyl.

\* \* \* \* \*